United States Patent
Kurasawa et al.

(10) Patent No.: US 6,787,650 B1
(45) Date of Patent: Sep. 7, 2004

(54) UREA COMPOUNDS, PROCESS FOR PRODUCING THE SAME AND USE THEREOF

(75) Inventors: Osamu Kurasawa, Ikeda (JP); Shinichi Imamura, Osaka (JP); Shohei Hashiguchi, Toyonaka (JP); Osamu Nishimura, Kawanishi (JP); Naoyuki Kanzaki, Ibaraki (JP); Masanori Baba, Kagoshima (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 10/089,961

(22) PCT Filed: Oct. 4, 2000

(86) PCT No.: PCT/JP00/06908

§ 371 (c)(1),
(2), (4) Date: Apr. 5, 2002

(87) PCT Pub. No.: WO01/25199

PCT Pub. Date: Apr. 12, 2001

(30) Foreign Application Priority Data

Oct. 5, 1999 (JP) .......................................... 11-284495

(51) Int. Cl.⁷ .................... C07D 417/00; C07D 413/00; C07D 711/26; C07D 711/22; C07D 401/00

(52) U.S. Cl. ........................... 544/60; 544/61; 544/111; 544/113; 544/114; 544/116; 544/117; 544/121; 544/127; 544/124; 544/128; 544/129; 544/180; 544/182; 544/224; 544/238; 544/242; 544/258; 544/283; 544/284; 544/353; 546/186; 546/187; 546/188; 546/190; 546/192; 546/194; 546/195; 546/196; 546/197; 546/200; 546/201; 546/202; 546/205; 546/207; 546/208; 546/209; 546/210; 546/213; 546/214

(58) Field of Search ................................ 546/231, 221, 546/216, 186, 187, 188, 190, 192, 194, 195, 196, 197, 200, 201, 202, 205, 207, 208, 209, 210, 213, 214; 544/60, 61, 111, 113, 114, 116, 117, 121, 122, 128, 129, 180, 182, 224, 238, 242, 258, 283, 284, 295, 353

(56) References Cited

U.S. PATENT DOCUMENTS 3,461,120 A   8/1969  Behn ........................ 260/240
4,835,157 A   5/1989  Press ........................ 514/258

FOREIGN PATENT DOCUMENTS

EP    0747357       12/1996
JP    09-255572     9/1997
WO    WO 99/04794   2/1999
WO    WO 00/35454   6/2000

Primary Examiner—Joseph Mekane
Assistant Examiner—Raymond Covington
(74) Attorney, Agent, or Firm—Mark Chao; Elaine M. Ramesh

(57) ABSTRACT

A compound of the formula:

(I)

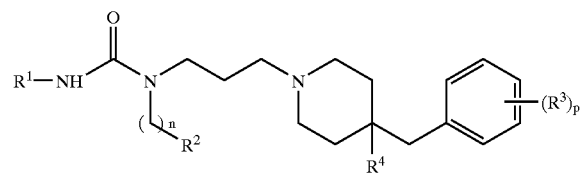

[wherein $R^1$ is a hydrocarbon group which may be substituted;

$R^2$ is a cyclic hydrocarbon group which may be substituted or a heterocyclic group which may be substituted;

$R^3$ is halogen atoms, a carbamoyl group which may be substituted, a sulfamoyl group which may be substituted, an acyl group derived from sulfonic acid, a $C_{1-4}$ alkyl group which may be substituted, a $C_{1-4}$ alkoxy group which may be substituted, an amino group which may be substituted, a nitro group or a cyano group;

$R^4$ is hydrogen atoms or a hydroxy group;

n is 0 or 1; and p is 0 or 1 to 4];

or a salt thereof, has potent CCR5 antagonistic activity and can be advantageously used as a medicament for inhibition of HIV infection to human peripheral blood mononuclear cells, especially for the treatment or prevention of AIDS.

11 Claims, No Drawings

UREA COMPOUNDS, PROCESS FOR PRODUCING THE SAME AND USE THEREOF

This application is the National Phase filing of International Patent Application No. PCT/JP00/06908, filed Oct. 4, 2000.

TECHNICAL FIELD

The present invention relates to urea compounds which are useful for the treatment of acquired immunodeficiency syndrome (AIDS), their production and use.

BACKGROUND ART

HIV (human immunodeficiency virus) protease inhibitors have been developed for the treatment of AIDS and use of the protease inhibitors in combination with two conventional HIV reverse transcriptase inhibitors has provided further progress in the treatment of AIDS. However, these drugs and their combination use are not sufficient to eradicate AIDS, and new anti-AIDS drugs based on different activities and mechanisms are therefore required.

CD4 is a known receptor from which HIV invades a target cell. Recently, CCR5 has been discovered as a second receptor of macrophage-tropic HIV. CCR5 is a G-protein-coupled chemokine receptor having seven transmembrane domains. This chemokine receptor is thought to play an essential role in establishment and spread of HIV infection. In fact, it is reported that a person who is resistant to HIV infection in spite of several exposures retains mutation of homo deletion of CCR5 gene. Therefore, a CCR5 antagonist is expected to be a new anti-HIV drug.

As chemokine receptor antagonists, there are known aromatic urea derivatives (J. Biol. Chem., 1998, 273, 10095–10098), benzodiazepine derivatives (Japanese unexamined patent publication No. 9-249570), cyclam derivatives (Nat. Med., 1998, 4, 72–77), spiro piperidine derivatives (WO98/25604, 25605), acridine derivatives (WO98/30218), xanthene derivatives (WO98/04554), haloperidol derivatives (J. Biol. Chem., 1998, 273, 15687–15692., WO98/24325, 02151), benzazocine-type compound (Japanese unexamined patent publication No. 9-25572), benzimidazole derivatives (WO98/06703), piperazine and diazepine derivatives (WO97/44329), 3-di-substituted piperidine derivatives (Japanese unexamined patent publication No. 9-249566), 4-substituted piperidine derivatives (WO99/04794), substituted pyrrolidine derivatives (WO99/09984, WO99/38514), etc. However, so far, there has been no report that a CCR5 antagonist is developed as a therapeutic agent of AIDS.

DISCLOSURE OF THE INVENTION

In order to investigate an anti-AIDS drug having CCR5 antagonistic activity, it is necessary to clone CCR5 gene from human tissue derived cDNA library, to ligate said gene with a vector for expression in animal cells, to introduce said gene into animal cells and to obtain cells expressing CCR5. In addition, with using this transformant, it is necessary to screen a compound which strongly inhibits binding of CC chemokine RANTES, which is natural ligand, to CCR5. However, so far there has been no report on a low molecule compound having CCR5 antagonistic activity.

The present inventors diligently made extensive studies on compounds having CCR5 antagonistic activity and, as a result, they found that a compound represented by the formula (I) or a salt thereof exhibits superior CCR5 antagonistic activity and is useful for inhibition of HIV infection to human peripheral blood mononuclear cells (especially medicament for treatment or prevention of AIDS), and also that the compound has superior absorbability when orally administered. Based on the finding, the present invention was accomplished.

More specifically, the present invention relates to:

(1) a compound of the formula:

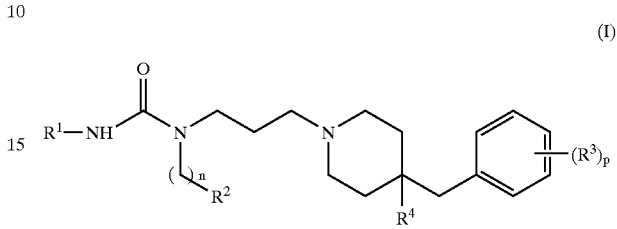

(I)

[wherein $R^1$ is a hydrocarbon group which may be substituted;
$R^2$ is a cyclic hydrocarbon group which may be substituted or a heterocyclic group which may be substituted;
$R^3$ is a halogen atom, a carbamoyl group which may be substituted, a sulfamoyl group which may be substituted, an acyl group derived from a sulfonic acid, a $C_{1-4}$ alkyl group which may be substituted, a $C_{1-4}$ alkoxy group which may be substituted, an amino group which may be substituted, a nitro group or a cyano group;
$R^4$ is a hydrogen atom or a hydroxy group;
n is an integer of 0 or 1;
p is an integer of 0 or 1 to 4];
or a salt thereof, (2) the compound as shown in the above (1), wherein $R^3$ is a halogen atom, a $C_{1-4}$ alkyl group which may be substituted, a $C_{1-4}$ alkoxy group which may be substituted, an amino group which may be substituted, a nitro group or a cyano group, (3) the compound as shown in the above (1), wherein $R^1$ is an alicyclic hydrocarbon group which may be substituted or an aryl group which may be substituted, (4) the compound as shown in the above (1), wherein $R^1$ is a hydrocarbon group which may be substituted by 1 to 4 substituent(s) selected from 1) a hydrocarbon group which may be substituted, 2) an heterocyclic group which may be substituted, 3) a $C_{1-4}$ alkoxy group which may be substituted, 4) a $C_{1-4}$ alkylthio group which may be substituted, 5) a $C_{2-6}$ alkoxycarbonyl group which may be substituted, 6) a $C_{1-6}$ alkanoyl group which may be substituted, 7) an amino group which may be substituted, 8) a cyclic amino group, 9) a halogen atom, 10) a nitro group, 11) a cyano group, 12) a carbamoyl group which may be substituted, 13) a sulfamoyl group which may be substituted and 14) an acyl group derived from a sulfonic acid, (5) the compound as shown in the above (1), wherein $R^1$ is a hydrocarbon group which may be substituted by 1 to 4 substituent(s) selected from 1) a hydrocarbon group which may be substituted, 2) a heterocyclic group which may be substituted, 3) a $C_{1-4}$ alkoxy group which may be substituted, 4) a $C_{1-4}$ alkylthio group which may be substituted, 5) a $C_{2-6}$ alkoxycarbonyl group which may be substituted, 6) an amino group which may be substituted, 7) a halogen atom, B) a nitro group and 9) a cyano group, (6) the compound as shown in the above (1), wherein $R^1$ is a hydrocarbon group which may be substituted by 1 to 4 substituent(s) selected from 1) a hydrocarbon group which may be substituted, 2) a heterocyclic group which may be substituted, 3) a $C_{1-4}$ alkylthio group which may be substituted, 4) a $C_{2-6}$ alkoxycarbonyl group which may be substituted, 5) an amino group which may be substituted, 6) a halogen atom and 7) a nitro group, (7) the compound as shown in the above (1), wherein $R^2$ is an cyclic hydrocarbon group which may be substituted, (8) the compound as shown in the above (1), wherein $R^3$ is a halogen, a carbamoyl group which may be substituted, a sulfamoyl group which may be substituted or an acyl group derived from a sulfonic acid, (9) the compound as shown in the above (1), wherein $R^3$ is a halogen,

(10) the compound as shown in the above (1), wherein $R^4$ is a hydrogen atom,

(11) the compound as shown in the above (1), wherein n is 0,

(12) the compound as shown in the above (1), wherein $R^1$ is a hydrocarbon group selected from Group 3 which may be substituted by member(s) selected from Group 1; $R^2$ is a cyclic hydrocarbon group selected from Group 10 which may be substituted by member(s) selected from Group 2, or a heterocyclic group selected from Group 4 which may be substituted by member(s) selected from Group 2; $R^3$ is a halogen atom, a carbamoyl group, a N-mono-substituted carbamoyl group which is substituted by a member selected from Group 11, a N,N-di-substituted carbamoyl group which is substituted by a member selected from Group 11 and a member selected from Group 14, a cyclic aminocarbonyl group selected from Group 17, a sulfamoyl group, N-mono-substituted sulfamoyl group which is substituted by a member selected from Group 11, a N,N-di-substituted sulfamoyl group which is substituted by a member selected from Group 11 and a member selected from Group 14, a cyclic aminosulfonyl group selected from Group 20, an acyl group derived from a sulfonic acid selected from Group 15, a $C_{1-4}$ alkyl group which may be substituted by member(s) selected from Group 2, a $C_{1-4}$ alkoxy group which may be substituted by member(s) selected from Group 2, an amino group which may be substituted by member(s) selected from Group 8, a cyclic amino group selected from Group 9, a nitro group or a cyano group.

[In the above,
Group I includes
1) a hydrocarbon group which selected from Group 3 which may be substituted by member(s) selected from Group 2, 2) a heterocyclic group which selected from Group 4 which may be substituted by member(s) selected from Group 2, 3) a $C_{1-4}$ alkoxy group which may be substituted by member(s) selected from Group 2, 4) a $C_{1-4}$ alkylthio group which may be substituted by member(s) selected from Group 2, 5) a $C_{2-6}$ alkoxycarbonyl group which may be substituted by member(s) selected from Group 2, 6) a $C_{1-6}$ alkanoyl group, 7) an amino group which may be substituted by member(s) selected from Group 8, 8) a cyclic amino group selected from Group 9, 9) a halogen atom, 10) a nitro group, 11) a cyano group, 12) a carbamoyl group, 13) a mono-substituted carbamoyl group which is substituted by a member selected from Group 11, 14) di-substituted carbamoyl group which is substituted by a member selected from Group 11 and a member selected Group 14, 15) a cyclic amino carbamoyl group selected from Group 17, 16) a sulfamoyl group, 17) a N-mono substituted sulfamoyl group which is substituted by a member selected from Group 11, 18) a N,N-di-substituted sulfamoyl group which is substituted by a member selected from Group 11 and a member selected Group 14, 19) an acyl group derived from a sulfonic acid selected from Group 19, Group 2 includes
1) a $C_{1-6}$ alkoxy group, 2) a halogen atom, 3) a $C_{1-6}$ alkyl group, 4) a $C_{1-4}$ alkynyl group, 5) an amino group, 6) a hydroxy group, 7) a cyano group and 8) an amidino group, Group 3 includes
1) a $C_{1-6}$ alkyl group, 2) a $C_{3-8}$ cycloalkyl group and 3) a $C_{6-14}$ aryl group, Group 4 includes
1) an aromatic monocyclic heterocyclic group selected from Group 5, 2) an aromatic condensed heterocyclic group selected from Group 6 and 3) a saturated or unsaturated non-aromatic heterocyclic group selected from Group 7, Group 5 includes
furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, Group 6 includes benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenathrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, Group 7 includes
oxylanyl, azetidinyl, oxetanyl, thietanyl, pyrrolidinyl, tetrahydrofuryl, thiolanyl, piperidinyl, tetrahydropyranyl, morpholinyl, thiomorpholinyl and piperazinyl, Group 8 includes
1) a $C_{1-6}$ alkyl, 2) a $C_{1-6}$ alkanoyl, 3) a $C_{7-13}$ arylcarbonyl, 4) an optionally halogenated $C_{2-6}$ alkoxycarbonyl, 5) a $C_{1-6}$ alkylimidoyl, 6) a formylimidoyl and 7) an amidino, Group 9 includes
1) 1-azetidinyl, 2) 1-pyrrolidinyl, 3) 1-piperidinyl, 4) 4-morpholinyl, 5) 1-piperazinyl and 6) 1-piperazinyl which may have a $C_{1-6}$ alkyl, a $C_{7-10}$ aralkyl and a $C_{6-10}$ aryl at 4-position, Group 10 includes
$C_{3-9}$ cycloalkyl, 1-indanyl, 2-indanyl, $C_{3-6}$ cycloalkenyl, $C_{4-6}$ cycloalkanedienyl and $C_{6-14}$ aryl, Group 11 includes
1) a $C_{1-6}$ alkyl group which may be substituted by member(s) selected from Group 12, 2) a $C_{3-6}$ cycloalkyl group which may be substituted by member(s) selected from Group 12, 3) a $C_{6-10}$ aryl group which may be substituted by member(s) selected from Group 12, 4) a $C_{7-10}$ aralkyl group which may be substituted by member(s) selected from Group 12, 5) a $C_{1-6}$ alkoxy group which may be substituted by member(s) selected from Group 12 and 6) a heterocyclic group selected from Group 13 which may be substituted by member(s) selected from Group 12, Group 12 includes 1) a hydroxy group, 2) an amino group, 3) an amino group which is mono or di-substituted by member(s) selected from Group 16, 4) a halogen atom, 5) a nitro group, 6) a cyano group, 7) a $C_{1-6}$ alkyl group which may be substituted by halogen atom(s) and 8) a $C_{1-6}$ alkoxy group which may be substituted by halogen atom(s), Group 13 includes 1) an aromatic heterocyclic group selected from Group 5 and Group 6 and 2) a saturated or unsaturated non-aromatic heterocyclic group selected from Group 7, each of which contains at least one heteroatom(s) selected from the group consisting of an oxygen atom, a sulfur atom and a nitrogen atom, Group 14 includes a $C_{1-6}$ alkyl group, a $C_{3-6}$ cycloalkyl group and a $C_{7-10}$ aralkyl group, Group 15 includes 1) a $C_{1-10}$ alkylsulfonyl which may be substituted by member(s) selected from Group 12, 2) a $C_{2-6}$ alkenylsulfonyl which may be substituted by member(s) selected from Group 12, 3) a $C_{2-6}$ alkynylsulfonyl which may be substituted by member(s) selected from Group 12, 4) a $C_{3-9}$ cycloalkylsulfonyl which may be substituted by member(s; selected from Group 12, 5) a $C_{3-9}$ cycloalkenylsulfonyl which may be substituted by member(s) selected from Group 12, 6) a $C_{6-14}$ arylsulfonyl which may be substituted by member(s) selected from Group 12 and 7) a $C_{7-10}$ aralkylsulfonyl which may be substituted by member(s) selected from Group 12, Group 16 includes a $C_{1-6}$ alkyl group, a $C_{1-6}$ alkanoyl, a $C_{7-13}$ arylcarbonyl and a $C_{1-6}$ alkylsulfonyl, Group 17 includes 1-azetidinylcarbonyl, 1-pyrrolidinylcarbonyl, 1-piperidinylcarbonyl, 4-morpholinylcarbonyl and 1-piperazinylcarbonyl which may be substituted by member(s) selected from Group 18, Group 18 includes a $C_{1-6}$ alkyl group, a $C_{7-10}$ aralkyl group and a $C_{6-10}$ aryl group, Group 19 includes a $C_{1-10}$ alkylsulfonyl which may be substituted by member(s) selected from Group 12, a $C_{2-6}$ alkenylsulfonyl which may be substituted by member(s) selected from Group 12, a $C_{2-6}$ alkynylsulfonyl which may be substituted by member(s) selected from Group 12, a $C_{3-9}$ cycloalkylsulfonyl which may be substituted by member(s) selected from Group 12, a $C_{3-9}$ cycloalkenylsulfonyl which may be substituted by member(s) selected from Group 12, a $C_{6-14}$ arylsulfonyl which may be substituted by member(s) selected from Group 12, and a $C_{7-10}$ aralkylsulfonyl which nay be substituted by member(s) selected from Group 12, and Group 20 includes 1-azetidinylsulfonyl, 1-pyrrolidinylsulfonyl, 1-piperidinylsulfonyl, 4-morpholinylsulfonyl and 1-piperazinylsulfonyl which may be substituted by member(s) selected from Group 18],

(13) the compound as shown in the above (1), wherein $R^1$ is a $C_{3-8}$ cycloalkyl group which may be substituted by member(s) selected from Group 1 ox a $C_{6-14}$ aryl group which may be substituted by member(s) selected from Group 1,

(14) the compound as shown in the above (12), wherein $R^1$ is 1) a $C_{6-14}$ aryl group which may be substituted by a halogen atom, a $C_{1-6}$ alkyl which may be substituted by halogen(s), a $C_{1-4}$ alkylthio, a nitro, 3 carbamoyl, a sulfamoyl or a $C_{1-6}$ alkylsulfonyl, 2) a $C_{1-6}$ alkyl group which may be substituted by (i) a $C_{2-6}$ alkoxycarbonyl group or (ii) a $C_{1-6}$ alkyl group which may be substituted by phenyl(s) which may be substituted by $C_{1-6}$ alkyl(s) or 3) a $C_{3-8}$ cycloalkyl group which may be substituted by (i) a halogen atom, (ii) a $C_{1-6}$ alkyl(s) which may be substituted by halogen(s) or (iii) a $C_{1-6}$ alkoxy group which may be substituted by halogen(s);

$R^2$ is a phenyl group which may be substituted by a halogen atom, a $C_{3-6}$ alkyl, a $C_{1-4}$ alkoxy or a cyano, a $C_{3-8}$ cycloalkyl group or a pyridyl group;

$R^3$ is (i) a halogen atom, (ii) a carbamoyl group, (iii) a sulfamoyl group which may have one or two $C_{1-6}$ alkyl(s) or $C_{3-6}$ cycloalkyl(s) at N-atoms, (iv) a cyclic aminosulfonyl group which is selected from Group 2D, (v) a $C_{1-6}$ alkylsulfonyl group or (vi) $C_{3-6}$ cycloalkylsulfonyl group;

$R^4$ is a hydrogen atom;

n is 0 or 1 and p is 0 or 1,

(15) the compound as shown in the above (12), wherein $R^1$ is 1) a phenyl which may be substituted by a halogen atom, a $C_{1-3}$ alkyl, trifluoromethyl, methoxy, trifluoromethoxy, methylthio or nitro, 2) a naphthyl, 3) a $C_{1-6}$ alkyl group which may be substituted by (i) a $C_{2-3}$ alkoxycarbonyl, (ii) phenyl or (iii) 3-isopropenylphenyl, or 4) cyclohexyl;

$R^2$ is a phenyl group which may be substituted by a halogen atom, methyl, methoxy or cyano, a cyclohexyl group or a 3-pyridyl group;

$R^3$ is (i) a halogen atom, (ii) a carbamoyl group, (iii) a 4-morpholinylsulfonyl group or (iv) a methylsulfonyl group, $R^4$ is a hydrogen atom;

n is 0 or 1; and p is 0 or 1,

(16) the compound as shown in the above (12), wherein $R^1$ is a phenyl group which may be substituted by a halogen atom or a $C_{1-3}$ alkyl; $R^2$ is a phenyl group which may be substituted by a halogen atom and methyl(s);

$R^3$ is (i) a halogen atom, (ii) a carbamoyl group, (iii) a sulfamoyl group which may be substituted by oe or two members selected from the group consisting of $C_{1-6}$ alkyl and $C_{3-6}$ cycloalkyl at N-atoms, (iv) a cyclic aminosulfonyl group selected from Group 20, (v) a $C_{1-6}$ alkylsulfonyl group or (vi) a $C_{3-6}$ cycloalkyl sulfonyl group;

$R^4$ is a hydrogen atom;

n is 0; and p is 0 or 1,

(17) the compound as shown in the above (1), which is N-[3-(4-benzyl-1-piperidinyl)propyl]-N'-(4- chlorophenyl)-N-phenylurea, N'-(4-chlorophenyl)-N-{3-[4-(4-fluorobenzyl)-1-piperidinyl]propyl}-N-phenylurea, N'-(4-chlorophenyl)-N-(3-{4-[4-(4-morpholinylsulfonyl)benzyl]-1-piperidinyl)propyl}-N-phenylurea, N'-(4-chlorophenyl)-N-(3-{4-[4-(4-methylsulfonyl)benzyl]-1-piperidinyl}propyl}-N-phenylurea, 4-{[1-(3-{[(4-chloroanilino)carbonyl]anilino}propyl)-4-piperidinyl]methyl}benzamide, or a salt thereof,

(18) a prodrug of the compound of the formula (I) or a salt thereof,

(19) a pharmaceutical composition containing a compound of the formula (I), a salt thereof or a prodrug thereof,

(20) the pharmaceutical composition as shown in the above (19), which is a chemokine receptor antagonist,

(21) the pharmaceutical composition as shown in the above (19), which is a CCR5 antagonist,

(22) the composition as shown in the above (19), which is for the treatment or prevention of infectious disease of HIV,

(23) the composition as shown in the above (19), which is for the treatment or prevention of AIDS,

(24) the composition as shown in the above (19), which is for the prevention of the progression of AIDS,

(25) the composition as shown in the above (22), further comprises a protease inhibitor and/or a reverse transcriptase inhibitor,

(26) the composition als shown in the above (25), wherein the reverse transcriptase inhibitor is zidovudine, didanosine, zalcitabine, lamivudine, stavudine, abacavir, nevirapine, delavirdine or efavirenz,

(27) the composition as shown in the above (25), wherein the protease inhibitor is saquinavir, ritonavir, indinavir, amprenavir or nelfinavir,

(28) use of a compound of the formula (I), a salt thereof or prodrug thereof for the manufacture of an antagonist of a chemokine receptor,

(29) use of a compound of the formula (I), a salt thereof or prodrug thereof for the manufacture of a CCR5 antagonist,

(30) use of a compound of the formula (I), a salt thereof or prodrug thereof, for the manufacture of a medicament for the treatment or prevention of infectious disease of HIV,

(31) use of a compound of the formula (I), a salt thereof or a prodrug thereof for the manufacture of a medicament for the treatment or prevention of infectious disease of HIV which is used in combination with a protease inhibitor and/or a reverse transcriptase inhibitor,

(32) a method for antagonizing CCR5 which comprises administering to a mammal in need thereof an effective amount of the compound of the formula (I), a salt thereof or a prodrug thereof,

(33) a method for producing a compound of the formula (I) or a salt thereof, which comprises reacting a compound of the formula:

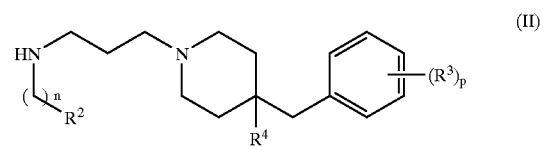

(II)

wherein each symbol has the meaning given above, or a salt thereof, with a compound of the formula:

$R^1$—N=C=O    (III)

wherein $R^1$ has the meaning given above, or a salt thereof,

(34) a method for producing a compound of the formula (I) or salt thereof, which comprises reacting a compound of the formula:

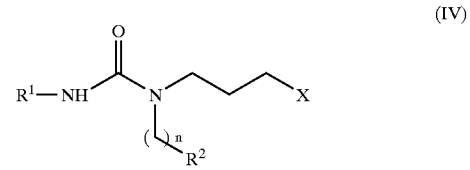

(IV)

wherein X is a leaving group, and other symbols have the meanings given above or a salt thereof, with a compound of the formula:

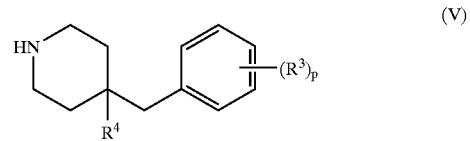

(V)

wherein each symbols has the same meaning given above, or a salt thereof in the presence of base.

Examples of the hydrocarbon group in the "a hydrocarbon group which may be substituted" represented by $R^1$ include, for example, an aliphatic hydrocarbon group, an alicyclic hydrocarbon group and an aryl group etc. Examples of the aliphatic hydrocarbon group include a $C_{1-6}$ alkyl group, for example, methyl, ethyl, n-propyl, isopropyl, n-butyl, isobutyl, sec-butyl, tert-butyl, n-pentyl, isopentyl, neopentyl, 1-methylpropyl, n-hexyl, isohexyl etc. Examples of the "alicyclic hydrocarbon group" include a $C_{3-8}$ cycloalkyl group such as cyclopropyl, cyclobutyl, cyclopentyl, cyclohexyl, cycloheptyl, cyclooctyl, etc. Examples of the aryl group include a $C_{6-14}$ aryl group such as phenyl, naphthyl (1-naphthyl, 2-naphthyl), etc, are preferred.

Examples of the substituent(s) in the "hydrocarbon group which may be substituted" represented by $R^1$ include a hydrocarbon group which may be substituted, a heterocyclic group which may be substituted, a halogen atom (e.g., fluorine, chlorine, bromine, iodine), a $C_{1-4}$ alkoxy group which may be substituted, a $C_{1-4}$ alkylthio group which may be substituted, a $C_{2-6}$ alkoxycarbonyl group which may be substituted, a $C_{1-6}$ alkanoyl group which may be substituted, an amino group which may be substituted, a nitro group, a cyano group, a carbamoyl group which may be substituted, a sulfamoyl group which may be substituted, an acyl group derived from a sulfonic acid, etc.

Examples of the hydrocarbon group(s) in the "hydrocarbon group which may be substituted" are those similar to the "hydrocarbon group" of the "hydrocarbon group which may be substituted", which is represented by $R^1$. Among these substituents, a $C_{1-6}$ alkyl group, a $C_{3-6}$ cycloalkyl group, a $C_{6-14}$ aryl group are preferred. These examples may include the substituents as mentioned above for $R^1$. Examples of the substituents in the "hydrocarbon group which may be substituted" include, for example, a lower alkoxy group (e.g., a $C_{1-6}$ alkoxy group such as methoxy, ethoxy, propoxy, etc.), a halogen atom (e.g., fluorine, chlorine, bromine, iodine, etc.), a lower alkyl group (e.g., a $C_{1-6}$ alkyl group such as methyl, ethyl, propyl, etc.), a lower alkenyl group (e.g., a $C_{1-4}$ alkenyl group such as vinyl, 1-propenyl, 2-propenyl, isopropenyl, buternyl, isobutenyl, etc.), an amino group, a hydroxy group, a cyano group, an anidino group etc. The hydrocarbon in "hydrocarbon which may be substituted" may have 1 to 3 substituent(s) as described above at any possible position.

Examples of the heterocyclic group in the "heterocyclic group which may be substituted" (the substituent in the "hydrocarbon group which may be substituted by $R^{1}$") include, for example, an aromatic heterocyclic group, saturated or unsaturated non-aromatic heterocyclic group (alicyclic heterocyclic group) etc., which contains, besides carbon atoms, at least one heteroatom(s) (preferably 1 to 4 heteroatom(s), more preferably, 1 to 2 heteroatom(s)) consisting of 1 to 3 kind(s) of heteroatom's) (preferably 1 to 2 kinds of heteroatom(s)) selected from an oxygen atom, a sulfur atom, a nitrogen atom, etc.

Examples of the "aromatic heterocyclic group" include an aromatic monocyclic heterocyclic group such as a 5 or 6-membered aromatic monoyclic heterocyclic group (e.g., furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl, etc.); an aromatic fused heterocyclic group such as a 8 to 12-membered aromatic fused heterocyclic group (e.g., benzofuranyl, isobenzofuranyl, benzothienyl, indolyl, isoindolyl, 1H-indazolyl, benzindazolyl, benzoxazolyl, 1,2-benzoisooxazolyl, benzothiazolyl, benzopyranyl, 1,2-benzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridaizinyl, etc.); etc., preferably, a heterocyclic group consisting of the above-mentioned 5- or 6-membered aromatic monocyclic heterocyclic group fused with a benzene ring or heterocyclic group consisting of the above-mentioned 5- or 6-membered aromatic monocyclic heterocyclic group fused with the same or different above-mentioned 5- or 6-membered aromatic monocyclic heterocyclic group, etc.

Examples of the "non-aromatic heterocyclic group" include a 3 to 8-membered (preferably 5 or 6-membered) saturated or unsaturated (preferably saturated) non-aromatic heterocyclic group (aliphatic heterocyclic group) such as oxiranyl, azetidinyl, oxetanyl, thiethanyl, pyrrolidinyl, tetrahydrofuryl, thiolanyl, piperidinyl, tetrahydropyranyl, morpholinyl, thiomorpholinyl, piperazinyl, etc.

Examples of the "substituent(s)" of the "heterocyclic group which may be substituted" (substituent(s) of the hydrocarbon group which may be substituted, which is represented by $R^1$) are those similar to the "substituent(s)" of the "hydrocarbon group which may be substituted" that is(are) the "substituent(s)" of the hydrocarbon group which may be substituted, which is represented by $R^1$.

Examples of "$C_{1-4}$ alkoxy group" in the "$C_{1-4}$ alkoxy group which may be substituted" include, for example, methoxy, ethoxy, n-propoxy, isopropoxy, n-butoxy, isobutoxy, tert-butoxy, etc. Example of "$C_{1-4}$ an alkylthio group" in the "$C_{1-4}$ an alkylthio group which may be substituted" include, for example, methylthio, ethylthio, n-propylthio, isopropylthio, n-butylthio, isobutylthio, tert-butylthio, etc. Example of the "$C_{2-6}$ alkoxycarbonyl group" in "$C_{2-6}$ alkoxycarbonyl group which may be substituted" include, for example, methoxycarbonyl, ethoxycarbonyl, n-propoxycarbonyl, isopropoxycarbonyl, n-butoxycarbonyl, isobutoxycarbonyl, tert-butoxycarbonyl, n-pentyloxycarbonyl, etc.

Examples of the "$C_{1-6}$ alkanoyl group" in the "$C_{1-6}$ alkanoyl group which may be substituted" include, for example, formyl, acetyl, propionyl, pivaloyl etc. Examples of the substituent in the "$C_{1-4}$ alkoxy group which may be substituted", "$C_{1-4}$ alkylthio group which may be substituted", and "$C_{1-6}$ alkoxycarbonyl group which may be substituted", "$C_{1-6}$ alkanoyl group which may be substituted" are those similar to the substituent(s) of the "hydrocarbon group which may be substituted", which are the substituent(s) of the "hydrocarbon group which may be substituted" represented by $R^1$.

Examples of the substituent(s) of the "amino group which may be substituted" include, for example, a lower alkyl group (e.g., a $C_{1-6}$ alkyl group such as methyl, ethyl, propyl, isopropyl, butyl, isobutyl, t-butyl, pentyl, hexyl, etc.), an acyl group derived from a carboxylic acid (e.g., a $C_{1-6}$ alkanoyl such as formyl, acetyl, propionyl, pivaloyl, etc.), a $C_{7-15}$ arylcarbonyl such as benzoyl, etc., an acyl group derived from a sulfonic acid (e.g., a $C_{1-6}$ alkylsulfonyl such as methylsulfonyl, ethylsulfonyl, etc.), an optionally halogenated $C_{2-6}$ alkoxycarbonyl (e.g., trifluoromethoxycarbonyl, 2,2,2-trifluoroethoxycarbonyl, trichloromethoxycarbonyl, 2,2,2-trichloroethoxycarbonyl, etc.), etc. In addition, the "amino group" in the "amino group which may be substituted" may be substituted with an imidoyl group which may be substituted (e.g., a $C_{1-6}$ alkylimidoyl, formylimidoyl, amidino, etc.), etc. Alternatively, two substituents of the amino group may form a cyclic amino group together with a nitrogen atom. Examples of said cyclic amino group include e.g. 3 to 8-membered (preferably 5 or 6-membered) cyclic amino group such as 1-azetidinyl, 1-pyrrolidinyl, 1-piperidinyl, 4-morpholinyl, 1-piperazinyl and 1-piperazinyl which may have at the 4-position a lower alkyl group (e.g., a $C_{1-6}$ alkyl group such as methyl, ethyl, propyl, isopropyl, butyl, t-butyl, pentyl, hexyl, etc.), an aralkyl group (e.g. a $C_{7-10}$ aralkyl group such as benzyl, phenethyl, etc.), an aryl group (e.g. a $C_{6-10}$ aryl group such as phenyl, 1-naphthyl, 2-naphthyl, etc.), etc.

Examples of the "carbamoyl group which may be substituted" include unsubstituted carbamoyl, a N-mono-substituted carbamoyl group and a N,N-di-substituted carbamoyl group.

The "N-mono-substituted carbamoyl group" is a carbamoyl group having one substituent on the nitrogen atom and the substituent include, for example, a lower alkyl group (e.g., a $C_{1-6}$ alkyl group such as methyl, ethyl, propyl, isopropyl, butyl, isobutyl, t-butyl, pentyl, hexyl, etc.), a cycloalkyl group (e.g., a $C_{3-6}$ cycloalkyl group such as cyclopropyl, cyclobutyl, cyclopentyl, cyclohexyl, etc.), an aryl group (e.g., a $C_{6-10}$ aryl group such as phenyl, 1-naphthyl, 2-naphthyl, etc.), an aralkyl group (e.g., a $C_{7-10}$ aralkyl group, preferably a phenyl-$C_{1-4}$ alkyl group such as benzyl, phenethyl, etc.), a heterocyclic group (e g., the above described "heterocyclic group" as the substituent of the "hydrocarbon group which may be substituted" represented by $R^1$, etc.), etc. The lower alkyl group, the cycloalkyl group, the aryl group, the aralkyl group and the heterocyclic croup as described above may have substituent(s), and the substituent(s) include, for example, a hydroxy group, an amino group which may be substituted [the amino group may have 1 or 2 substituent(s) (e.g. a lower alkyl group (e.g., a $C_{1-6}$ alkyl group such as methyl, ethyl, propyl, isopropyl, butyl, isobutyl, t-butyl, pentyl, hexyl, etc.), an acyl group (e.g., a $C_{1-6}$ alkanoyl such as formyl, acetyl, propionyl, pivaloyl, etc., an arylcarbonyl such as benzoyl, etc., a $C_{1-6}$ alkylsulfonyl such as methylsulfonyl, ethylsulfonyl, etc.), etc.)], a halogen atom (e.g., fluorine, chlorine, bromine, iodine, etc.), a nitro group, a cyano group, a lower alkyl group which may be substituted with 1 to 5 halogen atom(s) (e.g., fluorine, chlorine, bromine, iodine, etc.), a lower alkoxy group which may be substituted with 1 to 5 halogen atom(s) (e.g., fluorine, chlorine, bromine, iodine, etc.), etc. The lower alkyl group) includes, e.g. a $C_{1-6}$ alkyl group such as methyl, ethyl, n-prop)yl, isopropyl, n-butyl, isobutyl, sec-butyl, tert-butyl, pentyl, hexyl, etc. and in particular methyl, ethyl, etc. are preferable. Said lower alkoxy group include e.g. a $C_{1-6}$ alkoxy group such as methoxy, ethoxy, n-propoxy, isopropoxy, n-butoxy, isobutoxy, sec-butoxy, tert-butoxy, etc. and in particular methoxy, ethoxy, etc. are preferable. The above described lower alkyl group, cycloalkyl group, aryl group, aralkyl group and heterocyclic group may have 1, 2 or 3 (preferably 1 or 2) substituent(s).

The "N,N-di-substituted carbamoyl group" is a carbomoyl group having two substituents on the nitrogen atom. Examples of one of the substituents include the same as those of the above described "N-mono-substituted carbamoly group" and examples of the other substituent include e.g. a lower alkyl group (e.g., a $C_{1-6}$ alkyl group such as methyl, ethyl propyl, isopropyl, butyl, t-butyl, pentyl, hexyl, etc.), a $C_{3-6}$ cycloalkyl group (e.g., cyclopropyl, cyclobutyl, cyclopentyl, cyclohexyl, etc.), a $C_{7-10}$ aralkyl group (e.g., benxyl, phenethyl, etc., preferably phenyl-$C_{1-4}$ alkyl group, etc.), etc. In addition, two substituents of the "N,N-di-substituted carbamoyl group" may form a cyclic aminocarbonyl group together with a nitrogen atom. Examples of said cyclic aminocarbonyl group include, e.g., 3 to 8-membered (preferably 5 or 6-membered) cyclic aminocarbonyl group such as 1-azetidinylcarbonyl, 1-pyrrolidinylcarbonyl, 1-piperidinylcarbonyl, 4-morpholinylcarbonyl, 1-piperazinylcarbonyl and 1-piperazinylcarbonyl which may have a lower alkyl group (e.g., a $C_{1-6}$ alkyl group such as methyl, ethyl, propyl, isopropyl, butyl, t-butyl, pentyl, hexyl, etc.), an aralkyl group (e.g., a $C_{7-10}$ aralkyl group such as benzyl, phenethyl, etc.), an aryl group (e.g., a $C_{6-10}$ aryl group such as phenyl, 1-naphthyl, 2-naphthyl, etc.), etc. at the 4-position.

Examples of the "sulfamoyl group which may be substituted" include an unsubstituted sulfamoyl group, a N-mono-substituted sulfamoyl group and a N,N-di-substituted sulfamoyl group.

The "N-mono-substituted sulfamoyl group" is a sulfamoyl group having one substituent at the nitrogen atom, and examples of the substituent include those mentioned for the substituents of N-mono-substituted carbamoyl group.

The "N,N-di-substituted sulfamoyl group" is a sulfamoyl group having two substituents at the nitrogen atom, and examples of the substituents include those mentioned as the substituents of the N,N-di-substituted carbamoyl group.

Examples of the "acyl group derived from a sulfonic acid" include a sulfonyl group substituted by a hydrocarbon group, and preferably, include an acyl group such as $C_{1-10}$ alkylsulfonyl, $C_{2-6}$ alkenylsulfonyl, $C_{2-6}$ alkynylsulfonyl, $C_{3-9}$ cycloalkylsulfonyl, $C_{3-9}$ cycloalkenylsulfonyl, $C_{6-14}$ arylsulfonyl, $C_{7-10}$ aralkylsulfonyl. Examples of the $C_{1-10}$ alkyl include, for example, methyl, ethyl, propyl, isopropyl, butyl, isobutyl, t-butyl, pentyl, hexyl, heptyl, octyl, etc. Examples of the $C_{2-6}$ alkenyl include, for (example, vinyl, allyl, 1-propenyl, isopropenyl, 2-butenyl, 3-butenyl, 2-hexenyl, etc. Examples of $C_{2-6}$ alkynyl include, for example, ethynyl, 2-propynyl, 2-butynyl, 5-hexynyl, etc. Examples of the $C_{3-9}$ cycloalkyl include, for example, cyclopropyl, cyclobutyl, cyclopentyl, cyclohexyl, cyclooctyl, etc. Examples of the $C_{3-9}$ cycloalkenyl include, for example, 1-cyclopenten-1-yl, 2-cyclopenten-1-yl, 3-cyclopenten-1-yl, 3-cyclohexen-1-yl, 3-cycloocten-1-yl, etc. Examples of the $C_{6-14}$ aryl include, for example, phenyl, 1-naphthyl, 2-naphthyl, etc. Examples of the $C_{7-10}$ aralkylsulfonyl include, for example, benzyl, phenethyl, etc. These hydrocarbon groups which are the substituents of the sulfonyl may be substituted. Examples of these substituents include, for example, hydroxy group, amino group which may be substituted [(the amino group may be substituted by one or two $C_{1-6}$ alkyl(s) (e.g., methyl, ethyl, propyl, isopropyl, butyl, isobutyl, t-butyl, pentyl, hexyl, etc.), an acyl group (e.g., $C_{1-6}$ alkanoyl such as formyl, acetyl, propionyl, pivaloyl, etc., aryl carbonyl such as benzoyl, etc., $C_{1-6}$ alkylsulfonyl such as methylsulfonyl, ethylsulfonyl, etc.)), halogen atom (for example, fluorine, chlorine, bromine, iodine, etc.), nitro, cyano, lower alkyl which may be substituted by 1 to 5 halogen atom(s) (e.g. fluorine, chlorine, bromine, iodine, etc.), $C_{1-6}$ alkoxy which may be substituted by 1 to 5 halogen atom(s) (e.g. fluorine, chlorine, bromine, iodine, etc.). Examples of the lower alkyl group include, for example, $C_{1-6}$ alkyl groups such as methyl, ethyl, n-propyl, isopropyl, n-butyl, isobutyl, sec-butyl, tert-butyl, pentyl, hexyl, etc., and preferably include methyl, ethyl, etc. The lower alkoxy group includes, for example, $C_{1-6}$ alkoxy such as methoxy, ethoxy, n-propoxy, isopropoxy, n-butoxy, isobutoxy, sec-butoxy, tert-butoxy, etc, and preferably include methoxy, ethoxy, etc. Preferably, one, two or three (preferably one or two) from these substituents is(are) used, wherein the substituents may be the same or different.

"Cyclic hydrocarbon group" in the "cyclic hydrocarbon group which may be substituted" of $R^2$ include alicyclic hydrocarbon group and aryl group.

Examples of the "alicyclic hydrocarbon group" include, for example, a saturated or unsaturated alicyclic hydrocarbon group such as a cycloalkyl group, a cycloalkenyl group, a cycloalkanedienyl group, etc. Examples of the "cycloalkyl group" include, for example, a $C_{3-9}$ cycloalkyl (preferably, a $C_{3-8}$ cycloalkyl) such as cyclopropyl, cyclobutyl, cyclopentyl, cyclohexyl, cycloheptyl, cyclooctyl, cyclononyl, etc., and a fused ring suhc as 1-indanyl, 2-indanyl, etc. Examples of the "cycloalkenyl group" include , for example, a $C_{3-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl, etc. Examples of the "cycloalkanedienyl group" include, for example, a $C_{4-6}$ cycloalkanedienyl group such as 2,4-cyclopentanedien-1-yl, 2,4-cyclohexanedien-1-yl, 2,5-cyclohexanedien-1-yl, etc. In particular, a $C_{3-8}$ cycloalkyl is preferable.

Examples of the "aryl group" exemplified by the hydrocarbon group include, for example, a monocyclic or fused aromatic hydrocarbon group. Among others, a $C_{6-14}$ aryl group such as phenyl, naphthyl, anthryl, phenanthryl, acenaphthylenyl, 4-indanyl, 5-indanyl, etc. are preferable. In particular, phenyl, 1-naphthyl, 2-naphthyl, etc. are preferable.

Examples of the "substituent(s)" in the "cyclic hydrocarbon group which may be substituted" represented by $R^2$ are those similar to the "substituent" of the "hydrocarbon group which may be substituted" described as the substituent(s) of the hydrocarbon group which may be substituted, which are represented by $R^1$.

Examples of the "heterocyclic group which may be substituted" of $R^2$ are those similar to the "heterocyclic group which may be substituted" described as the substituent(s) of the "hydrocarbon group which may be substituted", which are represented by $R^1$.

The halogen atom represented by $R^3$ include, for example, fluorine, chlorine, bromine, iodine, etc.

The "carbomoyl group which may be substituted", "sulfamoyl group which may be substituted" and "acyl group derived from a sulfonic acid" represented by $R^3$ are those similar to the "carbamoyl group which may be substituted", "sulfamoyl group which may be substituted" and "acyl group derived from a sulfonic acid", which are represented by $R^1$.

Examples of the "$C_{1-4}$ alkyl group" of the "$C_{1-4}$ alkyl group which may be substituted" represented by $R^3$ include, for example, methyl, ethyl, n-propyl, isopropyl, n-butyl, isobutyl, tert-butyl. Examples of the "$C_{1-4}$ alkoxy group" of the "$C_{1-4}$ alkoxy group which may be substituted" represented $R^3$ include, for example, methoxy, ethoxy, propoxy, n-butoxy, isobutoxy, tert-butoxy.

Example of the substituent(s) in the "$C_{1-4}$ alkyl group which may be substituted" and "$C_{1-4}$ alkoxy group which may be substituted", which is represented by $R^3$ are those similar to the "substituent(s)" of the "hydrocarbon group which may be substituted" that is(are) the "substituent(s)" of "the hydrocarbon group which may be substituted", which is represented by $R^1$.

Examples of the substituents of "amino group which may be substituted" represented by $R^3$ include, for example, lower alkyl group (e.g., $C_{1-6}$ alkyl group such as methyl, ethyl, propyl, isopropyl, butyl, isobutyl, t-butyl, pentyl, hexyl, etc.), an acyl group derived from carboxylic acid (e.g., $C_{1-6}$ alkanoyl such as formyl, acetyl, propionyl, pivaloyl, etc.), for example, $C_{7-15}$ arylcarbonyl such as benzoyl, etc, an acyl group derived from sulfonic acid (e.g., $C_{1-6}$ alkylsulfonyl such as methylsulfonyl, ethylsulfonyl, etc.), an optionally halogenated $C_{1-6}$ alkoxy-carbonyl (e.g., trifluoromethoxycarbonyl, 2,2,2-trifluoroethoxycarbonyl, trichloromethoxycarbonyl, 2,2,2-trichloroethoxycarbonyl, etc.), etc. In addition, the "amino group" of the "amino group which may be substituted" may be substituted with an imidoyl group which may be substituted (e.g., a $C_{1-6}$ alkylimidoyl, formylimidoyl, amidino, etc.), etc. and two substituents of the "amino group" may form a cyclic amino group together with a nitrogen atom. Examples of said cyclic amino group include, for example, 3 to 8-membered (preferably, 5 or 6-membered) cyclic amino group such as 1-azetidinyl, 1-pyrrolidinyl, 1-piperidinyl, 4-morpholinyl, 1-piperazinyl and 1-piperazinyl which may have a lower alkyl group (e.g., a $C_{1-6}$ alkyl group such as methyl, ethyl, propyl, isopropyl, butyl, t-butyl, pentyl, hexyl, etc.), an aralkyl group (e.g., a $C_{7-10}$ aralkyl group such as benzyl, phenethyl, etc.), an aryl group (e.g., a $C_{6-10}$ aryl group such as phenyl, 1-naphthyl, 2-naphthyl, etc.), etc. at the 4-position.

Examples of the leaving group represented by X include, for example, a halogen atom (e.g., a chlorine atom, a bromine atom, an iodine atom, etc.), an alkyl or aryl sulfonyloxy group (e.g., methanesulfonyloxy, trifluoromethanesulfonyloxy, ethanesulfonyloxy, benzenesulfonyloxy, p-toluenesulfonyloxy, etc.), etc.

Examples of the salt of a compound of the formula (I) of the present invention include a salt with an acid, for example, a salt with inorganic acid (e.g., hydrochloric acid salt, sulfuric acid salt, hydrobromic acid salt, phosphoric acid salt, etc.), a salt of an organic acid (e.g., acetic acid salt, trifluoroacetic acid salt, succinic acid salt, maleic acid salt, fumaric acid salt, propionic acid salt, citric acid salt, tartaric acid salt, lactic acid salt, oxalic acid salt, methanesulfonic acid salt, p-toluenesulfonic acid salt, etc.), etc., a salt with a base (e.g., an alkali metal salt such as potassium salt, sodium salt, lithium salt, etc., an alkaline earth metal salt such as calcium salt, magnesium salt, etc., ammonium salt, a salt with an organic base such as trimethylamine salt, triethylamine salt, tert-butyl dimethyl amine salt, dibenzyl methylamine salt, benzyl dimethylamine salt, N,N-dimethylaniline salt, pyridine salt, quinoline salt, etc.).

The compound of the formula (I) or salt thereof may also be hydrated. Hereinafter the compound of the formula (I), its salt and its hydrate are referred to as Compound (I).

A prodrug of the Compound (I) of the present invention means a compound which is converted to the Compound (I) having inhibitory activity of CCR5 by a reaction due to an enzyme, an gastric acid, etc. in vivo.

Examples of the prodrug of the Compound (I) include a compound wherein an amino group of the Compound (I) is substituted with acyl, alkyl, phosphoric acid (e.g. a compound wherein an amino group of the Compound (I) is substituted with eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl, etc.); a compound wherein a hydroxy group of the Compound (I) is substituted with an acyl, an alkyl, a phosphoric acid group, a boric acid group (e.g. a compound wherein a hydroxy group of the Compound (I) is substituted with acetyl, palmitoyl, propanoyl, pivaloyl, succinyl, fumaryl, alanyl, dimethylaminomethylcarbonyl, etc.); a compound wherein a carboxyl group of the Compound (I) is modified to ester, amide (e.g. a compound wherein a carboxyl group of the Compound (I) is modified to ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. These prodrugs can be produced by per se known method.

The prodrug of the Compound (I) may be a compound which is converted into the Compound (I) under the physiological conditions as described in "Pharmaceutical Research and Development", Vol. 7 (Drug Design), pages 163–198 published in 1990 by Hirokawa Publishing Co. (Tokyo, Japan).

The prodrug of the Compound (I) may be distinct entity or in the form of a pharmaceutically acceptable salts. Examples of said salt include a salt with an inorganic base (e.g., an alkaline metal such as sodium, potassium, etc.; an alkaline earth metal such as (calcium, magnesium, etc.; transition metal such as zinc, iron, copper, etc.); an organic base (e.g., an organic amine such as trimethylamine, triethylamine, pyridine, picoline, ethanolamine, diethanolamine, triethanolamine, dicyclohexylamine, N,N'-dibenzylethylenediamine, etc.; a basic amino acid such as arginine, lysine, ornithine, etc.); etc.; when the prodrug of the Compound (I) has an acidic group such as a carboxyl group, etc.

Examples of said salt also include a salt with an inorganic acid or an organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.); an acidic amino acid such as aspartic acid, glutamic acid, etc.; etc., when the prodrug of the Compound (I) has a basic group such as an amino group, etc.

The prodrug of the Compound (I) may be hydrated or unhydrated.

The Compound (I) may have one or more asymmetric carbon(s) in the molecule. The compound of the present invention may have both R-configuration and S-configuration as to the asymmetric carbon(s).

Unless otherwise mentioned, the "lower" in "a lower alkyl group", "a lower alkoxy group", etc., throughout the present specification means a straight, branched or cyclic carbon chain having 1 to 6 carbon(s).

Among the compounds represented by the formulas (II) to (VI), the compound having a basic group or acidic group may form an acid addition salt or a salt with a base, respectively. Examples of the salt include those mentioned as the salt of the compound represented by the formula (I). Hereinafter the compounds represented by each formula and a salt thereof are referred to as Compound (symbol of the formula). For example, the compound represented by the formula (II) and salt thereof are simply referred to as Compound (II).

Compound (I) can, for example, be prepared by the following methods:

Production 1

As shown in the following formula, Compound (II) can be reacted with Compound (III) to give Compound (I).

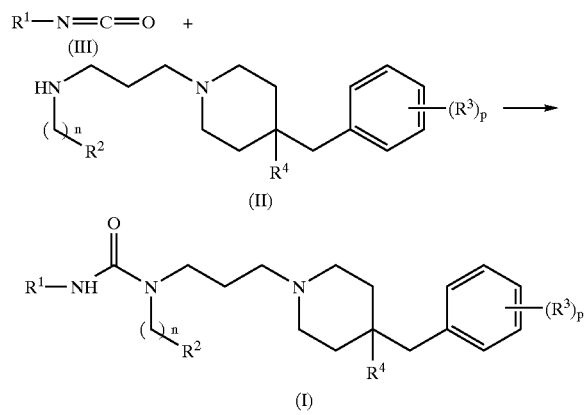

(In the above formulas, each symbol has the same meaning as defined above.)

The reaction is usually carried out in a solvent inert to the reaction. Examples of the solvent include an ether (e.g., ethyl ether, diisopropyl ether, dimethoxy ethane, tetrahydrofuran, dioxane, etc.), a halogenated hydrocarbon (e.g., dichloromethane, dicholoroethane, chloroform, etc.), an aromatic solvent (e.g., toluene, chlorobenzene, xylene, etc.), acetonitrile, N,N-dimethylformamide (DMF), acetone, methylethyl ketone, dimethylsulfoxide (DMSO), water, etc., or a mixed solvent thereof. Among them, acetonitrile, dichloromethane, chloroform, etc. are preferable. The reaction is usually carried out by using 1 to 5 equivalents), preferably 1 to 3 equivalents of Compound (III) relative to 1 equivalent of Compound (II). The reaction temperature ranges from −20° C. to 50° C., preferably 0° C. to room temperature, and reaction time is usually 5 minutes to 100 hours. The reaction may smoothly proceed by using a base. As the base, an inorganic base and an organic base can be used effectively. Examples of the inorganic base include a hydroxide, a hydride, a carbonate, a bicarbonate of alkaline metal or alkaline earth metal. Among them, potassium carbonate, sodium carbonate, sodium hydroxide, potassium hydroxide, sodium hydrogencarbonate, potassium hydrogencarbonate are preferable. Examples of the organic base preferably include a tertiary amine such as triethylamine.

Compound (II) can be produced, for example, by a method described in Synthetic Comm., 1991, 20, 3167–3180. That is, the above compound can be produced by the following method by applying an addition reaction of amines or amides to unsaturated bond.

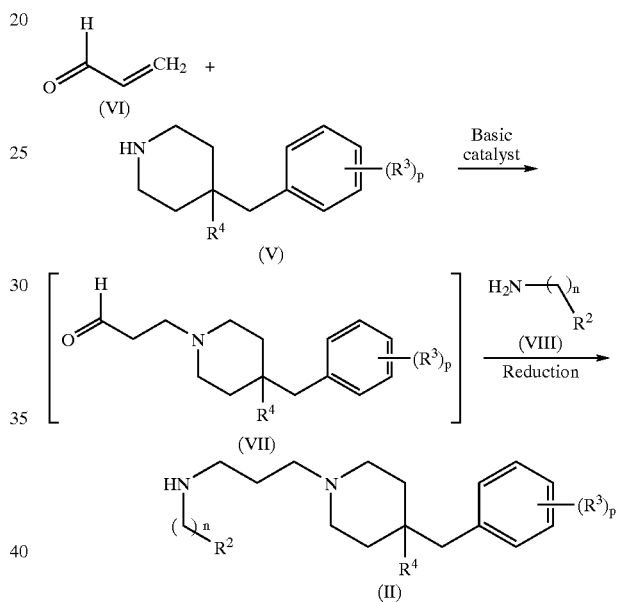

In the above formula, each symbol has the same meaning as defined above.

The compound can be produced by reacting acrolein (VI) with Compound (V), followed by reacting the resulting compound with Compound (VIII) under a condition of reduction. The reaction of Compound (VI) with Compound (V) is usually carried out in a solvent inert to the reaction in the presence of a base. Examples of the base include 1) a strong base such as hydride of alkali metal or alkaline earth metal (e.g., lithium hydride, sodium hydride, potassium hydride, calcium hydride, etc.), an amide of an alkali metal or an alkaline earth metal (e.g., lithium amide, sodium amide, lithium diisopropylamide, lithium dicyclohexylamide, lithium hexamethyldisilazide, sodium hexamethyldisilazide, potassium hexamethyldisilazide, etc.), a lower alkoxide of alkali metal or alkaline earth metal (e.g., sodium methoxide, sodium ethoxide, potassium t-butoxide, etc.), etc., 2) an inorganic base such as a hydroxide of an alkali metal or an alkaline earth metal (e.g., sodium hydroxide, potassium hydroxide, lithium hydroxide, barium hydroxide, etc.), a carbonate of an alkali metal or an alkaline earth metal (e.g., sodium carbonate, potassium carbonate, cesium carbonate, etc.), a bicarbonate of alkali metal or alkaline earth metal (e.g., sodium hydrogencarbonate, potassium hydrogencarbonate, etc.), etc., 3) an organic base, etc., such an amine as triethylamine, diisopropylethylamine, N-methylmorpholine, dimethylaminopyridine, DBU (1,8-diazabicyclo[5.4.0]-7-undecene), DBN (1,5-diazabicyclo[4.3.0]non-5-ene), etc., and such basic heterocyclic Compound, etc., as pyridine, imidazole, 2,6-lutidine, etc. Examples of the solvent include those mentioned in the reaction of Compound (II) with Compound (III). These solvents can be used solely or in combination. Compound (VII) can be obtained in the reaction.

Examples of the reducing agent for the reaction of Compound (VII) with Compound (VIII) include sodium borohydride, lithium borohydride, sodium cyanoborohydride, sodium triacetoxyborohydride, etc. The used amount of the reducing agent is usually in the range of 1 to 10 equivalents, preferably in the range of 1 to 4 equivalents relative to 1 equivalent of Compound (VII). The reaction temperature ranges −20 to 50° C., preferably 0° C. to room temperature, and reaction time is 0.5 to 24 hours.

Catalytic reduction reaction is carried out in the presence of a catalytic amount of a metal catalyst such as Raney nickel, platinum oxide, metallic palladium, palladium-carbon, etc., in an inert solvent (e.g., an alcohol such as methanol, ethanol, isopropanol, t-butanol, etc.), at room temperature to 100° C., under a hydrogen pressure of 1 to 100 atm for 1 to 48 hours.

Production 2

Compound (I) can be produced by reacting Compound (IV) with Compound (V) as shown below.

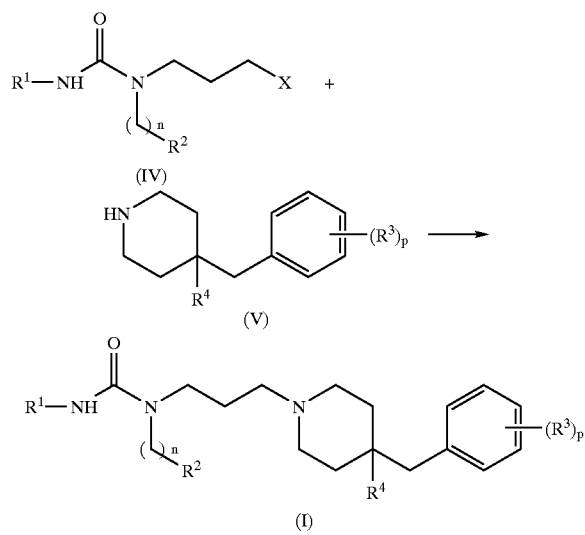

(In the above formulas, each symbol has the same meaning as defined above.)

The reaction can be carried out by a manner similar to that described in Organic Functional Group Preparations 2nd ed., (Academic Press, Inc.).

The reaction is usually carried out in a solvent inert to the reaction. Examples of the solvent include an alcohol, an ether, a halogen solvent, an aromatic solvent, acetonitrile, N,N-dimethylformamide (DMF), acetone, methylethyl ketone, dimethylsulfoxide (DMSO), etc. These solvents can be used solely or in combination. Among them, acetonitrile, dimethylformamide, acetone, ethanol, etc., are preferable. The reaction temperature ranges usually from room temperature to 100° C., preferably from room temperature to 50° C., and the reaction time is usually 0.5 to 1 day. In this reaction, a base is usually added in an amount of 1 to 3 equivalents relative to 1 equivalent of Compound (IV), but it is not essential. Examples of the base include those mentioned in the reaction of Compound (II) with Compound (III).

Compound (IV) used as a starting material in the reaction can be produced from Compound (III) by a known conventional method.

Production 3

Compound (I) can be produced by reacting a compound of the formula (IX) with a compound of the formula (V) under a reduction condition as shown below.

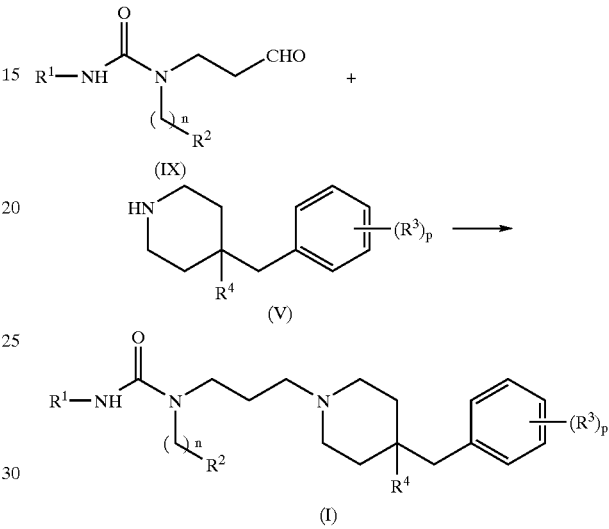

(In the above formulas, each symbol has the same meaning as defined above.)

The reaction is carried out by reacting Compound (IX) with Compound (V) in an appropriate solvent (e.g., water, an alcohol, an ether, a halogenated solvent, acetonitrile, or a mixed solvent of two or more of these solvents, etc.), if necessary, by the addition of acidic substance such as acetic acid, trifluoroacetic acid, etc., in the presence of 1 to 5 equivalents, preferably 1 to 1.5 equivalent of a reducing agent. The reducing agent and the reaction condition mentioned in Production 1 can be applied for this reaction.

Compound (IX) used as a starting material in the reaction can be produced from Compound (III) by a known conventional method.

The Compound (I) of the present invention has potent CCR antagonistic activity (in particular, potent CCR5 antagonistic activity) and therefore can be used for the treatment or prevention of various infectious diseases of HIV in human, for example, AIDS. The compound (I) of the present invention is low toxic and safely used.

The Compound (I) of the present invention can be used as a CCR5 antagonist, for example, a drug for treatment or prevention of AIDS or a drug for the prevention of the progression of AIDS.

The compound of the present invention can be formulated by mixing individually or simultaneously with pharmaceutically acceptable carriers, excipients, binders, diluents or the like, which can be administered orally or non-orally as a pharmaceutical composition. It is well absorbed by orally. It can be administrated as tablets, capsules, granules and powders.

The dose per day of the compound (I) varies depending on the condition and body weight of a patient, administration route, etc. Typical daily dose per adult patient (body weight:

50 Kg) for oral administration is about 5 to 1000 mg, preferably about 10 to 600 mg, more preferably about 10 to 300 mg, and in particular about 15 to 150 mg, as an active ingredient [the compound (I)] and the compound (I) is administered once or 2 to 3 times per day.

The compound (I) of the present invention may be used in combination with other drugs for the treatment or prevention of infectious disease of HIV (in particular, a drug for the treatment or prevention of AIDS). In this case, these drugs can be formulated by mixing individually or simultaneously with pharmaceutically acceptable carriers, excipients, binders, diluents or the like, which can be administered orally or non-orally as a pharmaceutical composition for the treatment or prevention of infectious disease of HIV. In the case of formulating these effective components individually, while the individually formulated agents can be administered in the form of their mixture prepared by using e.g. a diluent when administered, the individually formulated agents can also be administered separately or simultaneously or with time intervals to the one and same subject. A kit for administering the individually formulated effective components in the form of their mixture prepared by using e.g. a diluent when administered (e.g. a kit for injection which comprises two or more ampoules each comprising a powdery component and a diluent for mixing and dissolving two or more components when administered, etc.), a kit for administering the individually formulated agents simultaneously or with time intervals to the one and the same subject (e.g. a kit for tablets to be administered simultaneously or with time intervals, characterized by having two or more tablets each comprising an agent and said tablets being put in one or separate bags and, if necessary, a column to describe time to be administered each agent, etc.), etc. are also included by the pharmaceutical composition of the present invention.

Example of the other pharmaceutical agent for the treatment or prevention of infectious disease of HIV to be used in combination with the compound (I) of the present invention include nucleoside reverse transcriptase inhibitor such as zidovudine, didanosine, zalcitabine, lamivudine, stavudine, abacavir, adefovir, adefovir dipivoxil, fozivudine tidoxil, etc.; non-nucleoside reverse transcriptase inhibitor (including an agent having anti-oxidative activity such as immunocal, oltipraz, etc.) such as nevirapine, delavirdine, efavirenz, loviride, immunocal, oltipraz, etc.; protease inhibitors such as saquinavir, ritonavir, indinavir, nelfinavir, amprenavir, palinavir, lasinavir, etc.; etc.

As the nucleoside reverse transcriptase inhibitor, zidovudine, didanosine, zalcitabine, lamivudine, stavudine, etc. are preferable; as the non-nucleoside reverse transcriptase inhibitor, nevirapine, delavirdine, etc. are preferable; and as the protease inhibitor, saquinavir, ritonavir, indinavir, nelfinavir, etc. are preferable.

The compound (I) of the present invention may be used in combination with, for example, CXCR4 antagonist (CXCR4 being a second receptor of T cell-tropic HIV-1) such as AMD-3100, etc., an antibody against HIV-1 surface antigen, HIV-1 vaccine, etc., in addition to the above-mentioned protease inhibitor, reverse transcriptase inhibitor, etc.

When the compound (I) is used in combination with a reverse transcriptase inhibitor and/or a protease inhibitor, the dose of the reverse transcriptase inhibitor or the protease inhibitor ranges, for example, from about 1/200 to 1/2 or more of usual dose to about 2 to 3 times or less of usual dose. In case that two or more drugs are used in combination, each dose of the drugs is appropriately adjusted if one drug affects metabolism of the other drug, while each dose of the drugs when they are used in combination is generally the same as the dose when they are used alone.

Typical daily dose of the reverse transcriptase inhibitor and the protease inhibitor is as follows:

| | |
|---|---|
| zidovudine | : 100 mg |
| didanosine | : 125 to 200 mg |
| zalcitabine | : 0.75 mg |
| lamivudine | : 150 mg |
| stavudine | : 30 to 40 mg |
| saquinavir | : 600 mg |
| ritonavir | : 600 mg |
| indinavir | : 800 mg |
| nelfinavir | : 750 mg |

In case of combination use of the compound (I) with a reverse transcriptase inhibitor and/or a protease inhibitor preferred embodiments are shown below.

(i) A drug containing about 10 to 300 mg of the compound (I) and a drug containing about 50 to 200 mg of zidovudine to one adult patient (body weight: 50 Kg) are administered. Each of the drugs may be administered to the one and the same subject simultaneously or with time intervals of 12 hours or less.

(ii) A drug containing about 10 to 300 mg of the compound (I) and a drug containing about 300 to 1200 mg of saquinavir to one adult patient (body weight: 50 Kg) are administered. Each of the drugs may be administered to the one and the same subject simultaneously or with time intervals of 12 hours or less.

BEST MODE FOR CARRYING OUT THE INVENTION

The present invention is hereinafter described in more detail by means of the following Example, Reference Example, Test Example and Formulation Example, which are mere examples of the present invention and are not construed as limitative to the present invention.

The following gene manipulation is carried out in accordance with methods described in textbook (Maniatis et al., Molecular Cloning, Cold Spring Harbor Laboratory, 1989) or protocol attached to reagents.

In the following Reference Examples and Examples, silica gel 60 (Merck, 70–230 or 230–400 mesh) was used as packing for column chromatography. Melting point was measured by using Yanaco MP-J3.

$^1$H NMR spectra were measured using tetramethylsilane as an internal standard with a Gemini 200 spectrometer (Varian, 200 MHz). Mass spectrum (APCI-MS) was measured by using Platform II (Micromass).

Preparative HPLC was conducted under the following condition.

Instrument: combinatorial chromatography system (Gilson)

Column: YMC CombiPrep ODS-A, 50×20 mm, S-5 $\mu$m

Eluant: A) 0.1% solution of trifluoroacetic acid in water, B) 0.1% solution of trifluoroacetic acid in acetonitrile 0.00 min (A/B=90/10), 1.20 min (A/B=90/10), 4.40 min (A/B=0/100), 5.60 min (A/B=0/100)

Amount injected: 500 $\mu$l, Flow Rate: 25 ml/min,

Detection: UV 220 nm

HPLC analysis was conducted under the following condition.

Instrument: LC-10Avp system (Shimadzu)

Column: CAPCELL PAK C$_{18}$ UG120, 50×2.0 mm, S-3 μm

Eluant: A) 0.1% solution of trifluoroacetic acid in water, B) 0.1% solution of trifluoroacetic acid in acetonitrile 0.00 min (A/B=90/10), 4.00 min (A/B=5/95), 5.50 min (A/B=5/95), 5.51 min (A/B=90/10), 8.00 min (A/B=90/10)

Flow Rate: 0.5 ml/min, Detection:UV 220 nm

REFERENCE EXAMPLE 1

N-[3-(4-Benzyl-1-piperidinyl)propyl]aniline dihydrochloride

A solution of acrolein (90%, 18.69 g, 300 mmol) in THF (60 ml) was dropwise added to a solution of 4-benzylpiperidine (52.58 g, 300 mmol) and DBU (0.449 ml, 3.0 mmol) in THF (600 ml) for 10 minutes at −20° C. under stirring. The mixture was stirred for 1 hour raising the temperature from −20° C. to −10° C. Aniline (27.94 g, 300 mmol) and triacetoxy sodium borohydride (127.16 g, 600 mmol) were added to the reaction mixture successively at −10° C. The mixture was stirred for 19 hours raising the temperature to room temperature. An aqueous solution of 2N sodium hydroxide (900 ml) was added to the reaction mixture under ice cooling, and the mixture was stirred for 30 minutes and extracted with diethyl ether (400 ml, 200 ml×2). The organic phase was dried over magnesium sulfate (anhydrous) and concentrated under reduced pressure. The residue was dissolved in 2-propanol (400 ml), and 4N hydrogen chloride in ethyl acetate (200 ml) was added to the solution with stirring. The resulting precipitate was collected by filtration. The precipitate was washed with 2-propanol (100 ml×3) and dried under reduced pressure to obtain the title compound as a white crystal (75.66 g, 198 mmol). Yield 66%.

Melting Point 217° C. (dec.).

$^1$H NMR (DMSO-d$_6$) δ 1.4–1.9 (5H, m), 2.0–2.25 (2H, m), 2.45–2.6 (2H, m), 2.83 (2H, br t, J=11.4 Hz), 3.12 (2H, br t, J=7.2 Hz), 3.29 (2H, br t, J=6.9 Hz), 3.41 (2H, br d, J=12.6 Hz), 7.05–7.5 (10H, m).

Anal. Calcd for C$_{21}$H$_{28}$N$_2$.2HCl.0.5H$_2$O: C, 64.61; H, 8.00; N, 7.18. Found: C, 64.71; H, 7.92; N, 7.32.

Free base (N-[3-(4-benzyl-1-piperidinyl)propyl]aniline).

$^1$H NMR (CDCl$_3$) δ 1.05–1.85 (9H, m), 2.34 (2H, t, J=6.8 Hz), 2.46 (2H, d, J=6.6 Hz), 2.83 (2H, br d, J=11.8 Hz), 3.06 (2H, t, J=6.4 Hz), 6.45–6.65 (3H, m), 7.0–7.25 (7H, m).

REFERENCE EXAMPLE 2

N-[3-(4-Benzyl-1-piperidinyl)propyl]-3-chloroaniline dihydrochloride

Using 3-chloroaniline, the title compound was synthesized in a manner similar to Reference Example 1. Yield 41%.

Melting Point 202° C. (dec.).

$^1$H NMR (DMSO-d$_6$) δ 1.53–2.01 (7H, m), 2.50–2.55 (2H, m), 2.66–2.92 (2H, m), 3.08–3.20 (4H, m), 3.38–3.44 (2H, m), 6.61–6.69 (3H, m), 7.07–7.30 (6H, m).

Anal. Calcd for C$_{21}$H$_{27}$ClN$_2$.2HCl.0.1H$_2$O: C, 60.39; H, 7.04; N, 6.71. Found: C, 60.33; H, 6.93; N, 6.84.

REFERENCE EXAMPLE 3

N-[3-(4-Benzyl-1-piperidinyl)propyl]-3,4-dichloroaniline dihydrochloride

Using 3,4-dichloroaniline, the title compound was synthesized in a manner similar to Reference Example 1. Yield 53%.

Melting Point 203° C. (dec.).

$^1$H NMR (DMSO-d$_6$) δ 1.49–1.76 (5H, m), 1.91–1.96 (2H, m), 2.50–2.55 (2H, m), 2.79–3.17 (6H, m), 3.38–3.44 (2H, m), 6.68 (1H, dd, J=2.8, 8.8 Hz), 6.75 (1H, d, J=2.6 Hz), 7.17–7.30 (6H, m).

Anal. Calcd for C$_{21}$H$_{26}$Cl$_2$N$_2$.2HCl.0.5H$_2$O: C, 54.92; H, 6.36; N, 6.10. Found: C, 55.11; H, 6.64; N, 6.37.

REFERENCE EXAMPLE 4

N-[3-(4-Benzyl-1-piperidinyl)propyl]-4-methylaniline dihydrochloride

Using p-toluidine, the title compound was synthesized in a manner similar to Reference Example 1. Yield 57%.

Melting Point 182–192° C. (dec.).

$^1$H NMR (DMSO-d$_6$) δ 1.4–1.9 (5H, m), 2.0–2.25 (2H, m), 2.31 (3H, s), 2.45–2.6 (2H, m), 2.7–2.95 (2H, m), 2.95–3.55 (6H, m), 7.1–7.45 (9H, m).

Anal. Calcd for C$_{22}$H$_{30}$N$_2$.2HCl.0.5H$_2$O: C, 65.34; H, 8.22; Cl, 17.53; N, 6.93. Found: C, 65.24; H, 8.38; Cl, 17.37; N, 6.98.

REFERENCE EXAMPLE 5-1

4-(4-Fluorobenzyl)piperidine hydrochloride

4-Fluorobenzylbromide (100 g) and triethyl phosphite (120 ml) were mixed and the mixture was stirred for 22 hours at 150° C. The obtained reaction mixture was distilled under reduced pressure (bp 115–120° C./1.5 mmHg) to give diethyl 4-fluorobenzyl phosphonate (125 g).

60% Sodium hydride (oily, 9.75 g) was added to a solution of diethyl 4-fluorobenzyl phosphonate (60.8 g) and 15-crown-5 (4 ml) in THF (400 ml) with stirring under ice cooling, and the mixture was stirred for 30 minutes at the same temperature. A solution of 1-tert-butoxycarbonyl-4-piperidone (42.0 g) in THF (150 ml) was dropwise added to the mixture with stirring under ice cooling, and the mixture was stirred for 22 hours at room temperature. Under ice cooling, water was added to the mixture and the mixture was extracted with ethyl acetate. The organic phase was washed with saturated aqueous solutions of sodium bicarbonate and saturated brine in order. The organic phase was dried over magnesium sulfate (anhydrous) and concentrated under reduced pressure. The residue was subjected to column chromatography (silica gel 650 g, hexane/ethyl acetate=30/1→10/1). The objective fraction was concentrated under reduced pressure to give 1-tert-butoxycarbonyl-4-(4-fluorobenzylidene)piperidine (47.0 g).

$^1$H NMR (CDCl$_3$) δ 1.48 (9H, s), 2.32–2.44 (4H, m), 3.37–3.53 (4H, m), 6.31 (1H, s), 7.00–7.19 (4H, m).

1-tert-Butoxycarbonyl-4-(4-fluorobenzylidene)piperidine (47.0 g) was dissolved in methanol (450 ml). 10% Palladium carbon (containing 50% water, 4.7 g) was added to the solution and the mixture was subjected to catalytic hydrogenation for 5 hours. The catalyst was filtered off and the filtrate was concentrated under reduced pressure to give 1-tert-butoxycarbonyl-4-(4-fluorobenzyl)piperidine (39.9 g).

$^1$H NMR (CDCl$_3$) δ 1.08–1.64 (14H, m), 2.49–2.69 (4H, m), 4.04–4.10 (2H, m), 6.92–7.12 (4H, m).

A solution of 4N hydrogen chloride in ethyl acetate (100 ml) was added to 1-tert-butoxycarbonyl-4-(4-fluorobenzyl) piperidine (39.9 g) and the solution was stirred for an hour at room temperature. The reaction mixture was concentrated under reduced pressure, then diethyl ether was added thereto. The resulting precipitate was collected by filtration, washed with diethyl ether, and dried under reduced pressure to give the title compound (30.1 g).

$^1$H NMR (CDCl$_3$) δ 1.70–1.81 (5H, m), 2.52–2.59 (2H, m), 2.71–2.89 (2H, m), 3.42–3.59 (2H, m), 6.93–7.07 (4H, m).

REFERENCE EXAMPLE 5-2

4-(4-Fluorobenzyl)piperidine

An aqueous solution of 1N sodium hydroxide (66 ml) was added to the compound obtained in Reference Example 5-1 (5.05 g), and the mixture was extracted with diethyl ether. The organic phase was dried over magnesium sulfate (anhydrous) and concentrated under reduced pressure to give the title compound.

$^1$H NMR (CDCl$_3$) δ 1.0–1.35 (2H, m), 1.35–1.7 (3H, m), 2.45–2.65 (2H, m), 2.49 (2H, d, J=6.6 Hz), 2.95–3.1 (2H, m), 6.95 (2H, t, J=8.8 Hz), 7.0–7.15 (2H, m).

REFERENCE EXAMPLE 5-3

N-{3-[4-(4-Fluorobenzyl)-1-piperidinyl]propyl}aniline dihydrochloride

Using the compound obtained in Reference Example 5-2, the title compound was obtained in a manner similar to Reference Example 1. Yield 54%.

Melting Point 230° C. (dec.).

$^1$H NMR (DMSO-d$_6$) δ 1.35–1.9 (5H, m), 1.95–2.2 (2H, m), 2.45–2.6 (2H, m), 2.83 (2H, br t, J=11.5 Hz), 3.11 (2H, br t, J=7.4 Hz), 3.24 (2H, br t, J=6.8 Hz), 3.42 (2H, br d, J=10.6 Hz), 6.9–7.2 (9H, m).

REFERENCE EXAMPLE 6

3,4-Dichloro-N-{3-[4-(4-fluorobenzyl)-1-piperidinyl]-propyl}aniline dihydrochloride Using the compound obtained in Reference Example 5-2 and 3,4-dichloroaniline, the title compound was obtained in a manner similar to Reference Example 1. Yield 48%.

Melting Point 203–209° C. (dec.).

$^1$H NMR (DMSO-d$_6$) δ 1.35–2.05 (7H, m), 2.45–2.6 (2H, m), 2.6–3.3 (6H, m), 3.41 (2H, br d, J=10.6 Hz), 6.57 (1H, dd, J=2.7, 8.8 Hz), 6.75 (1H, d, J=2.7 Hz), 7.05–7.3 (5H, m).

Anal. Calcd for C$_{21}$H$_{25}$Cl$_2$FN$_2$·2HCl·0.5H$_2$O: C, 52.85; H, 5.91; N, 5.87. Found: C, 52.90; H, 6.12; N, 5.94.

REFERENCE EXAMPLE 7

N-[3-(4-Benzyl-1-piperidinyl)propyl]benzylamine

A solution of acrolein (90%, 3.2 g, 57 mmol) in THF (2 ml) was dropwise added to a solution of 4-benzylpiperidine (10.0 g, 57 mmol) and DBU (85 μl, 0.57 mmol) in THF (10 ml) for 10 minutes at −20° C. under stirring. The mixture was stirred for an hour raising the temperature from −20° C. to −10° C. Benzylamine (6.1 g, 57 mmol) and triacetoxy sodium borohydride (24.2 g, 114 mmol) were added to the reaction mixture successively at −10° C., and the mixture was stirred for 19 hours raising the temperature to room temperature. An aqueous solution of 2N sodium hydroxide (100 ml) was added to the reaction mixture under ice cooling and the mixture was stirred for 30 minutes, and extracted with diethyl ether (100 ml, 80 ml×2). The organic phase was dried over magnesium sulfate (anhydrous), then concentrated under reduced pressure. The residue was dissolved in 2-propanol (50 ml) and to the solution was added a solution of 4N hydrogen chloride in ethyl acetate (50 ml) with stirring. The resulting precipitate was collected by filtration. The precipitate was washed with 2-propanol (20 ml×3) and dried under reduced pressure to give the title compound as a white crystal (6.5 g).

To the obtained white crystal (2.0 g) was added an aqueous solution of 1N sodium hydroxide (10 ml) to dissolve the crystal, and the solution was extracted with ethyl acetate (10 ml, 8 ml×2). The organic phase was dried over magnesium sulfate (anhydride) and concentrated under reduced pressure to give the title compound (1.6 g) as a colorless oil.

$^1$H NMR (CDCl$_3$) δ 1.30 (2H, dt, J=11.8 Hz, 2.4 Hz), 1.49 (1H, m), 1.59–1.89 (6H, m), 2.35 (2H, t, J=7.8 Hz), 2.52 (2H, d, J=6.8 Hz), 2.66 (2H, t, J=6.8 Hz), 2.90 (2H, d, J=11.8 Hz), 3.78 (2H, s), 7.12–7.33 (10H, m).

MS (APCI$^+$) 323 (M+1).

REFERENCE EXAMPLE 8

N-[3-(4-Benzyl-1-piperidinyl)propyl]-4-fluorobenzylamine

Using 4-fluorobenzylamine, the title compound was synthesized in a manner similar to Reference Example 7.

$^1$H NMR (CDCl$_3$) δ 1.26 (2H, dt, J=12.0 Hz, 2.6 Hz), 1.51 (1H, m), 1.59–1.92 (6H, m), 2.39 (2H, t, J=7.0 Hz), 2.49 (2H, d, J=6.8 Hz), 2.66 (2H, t, J=7.0 Hz), 2.91 (2H, d, J=11.8 Hz), 3.74 (2H, s), 6.94–7.32 (9H, m).

MS (APCI$^+$) 341 (M+1).

REFERENCE EXAMPLE 9

N-[3-(4-Benzyl-1-piperidinyl)propyl]-3-chlorobenzylamine

Using 3-chlorobenzylamine, the title compound was synthesized in a manner similar to Reference Example 7.

$^1$H NMR (CDCl$_3$) δ 1.29 (2H, dt, J=12.0 Hz, 3.6 Hz), 1.41–1.91 (7H, m), 2.38 (2H, t, J=7.6 Hz), 2.51 (2H, d, J=6.6 Hz), 2.67 (2H, t, J=6.6 Hz), 2.92 (2H, d, J=11.6 Hz), 3.76 (2H, s), 7.11–7.33 (9H, m).

MS (APCI$^+$) 357 (M+1).

REFERENCE EXAMPLE 10

N-[3-(4-Benzyl-1-piperidinyl)propyl]-3,4-dichlorobenzylamine

Using 3,4-dichlorobenzylamine, the title compound was synthesized in a manner similar to Reference Example 7.

$^1$H NMR (CDCl$_3$) δ 1.29 (2H, dt, J=12.0 Hz, 2.6 Hz), 1.52 (1H, m), 1.60–1.92 (6H, m), 2.39 (2H, t, J=7.4 Hz), 2.51 (2H, d, J=6.8 Hz), 2.65 (2H, t, J=7.4 Hz), 2.92 (2H, d, J=11.8 Hz), 3.73 (2H, s), 7.10–7.43 (8H, m).

MS (APCI$^+$) 391 (M+1).

REFERENCE EXAMPLE 11

N-[3-(4-Benzyl-1-piperidinyl)propyl]-2,6-difluorobenzylamine

Using 2,6-difluorobenzylamine, the title compound was synthesized in a manner similar to Reference Example 7.

$^1$H NMR (CDCl$_3$) δ 1.24 (2H, dt, J=12.0 Hz, 2.6 Hz), 1.52 (1H, m), 1.55–1.90 (6H, m), 2.42 (2H, t, J=7.0 Hz), 2.52

(2H, d, J=6.8 Hz), 2.69 (2H, t, J=7.0 Hz), 2.94 (2H, d, J=11.8 Hz), 3.76 (2H, s), 6.91–7.38 (8H, m).

MS (APCI$^+$) 359 (M+1).

REFERENCE EXAMPLE 12

N-[3-(4-Benzyl-1-piperidinyl)propyl]-2-chlorobenzylamine

Using 2-chlorobenzylamine, the title compound was synthesized in a manner similar to Reference Example 7.

$^1$H NMR (CDCl$_3$) δ 1.23 (2H, dt, J=11.8 Hz, 2.6 Hz), 1.52 (1H, m), 1.57–1.89 (6H, m), 2.37 (2H, t, J=7.0 Hz), 2.48 (2H, d, J=6.8 Hz), 2.63 (2H, t, J=7.0 Hz), 2.91 (2H, d, J=11.8 Hz), 3.72 (2H, s), 6.95–7.40 (9H, m).

MS (APCI$^+$) 357 (M+1).

REFERENCE EXAMPLE 13

N-[3-(4-Benzyl-1-piperidinyl)propyl]-4-chlorobenzylamine

Using 4-chlorobenzylamine, the title compound was synthesized in a manner similar to Reference Example 7.

$^1$H NMR (CDCl$_3$) δ 1.26 (2H, dt, J=12.0 Hz, 2.8 Hz), 1.51 (1H, m), 1.59–1.90 (6H, m), 2.39 (2H, t, J=7.0 Hz), 2.51 (2H, d, J=6.8 Hz), 2.66 (2H, t, J=7.0 Hz), 2.93 (2H, d, J=11.8 Hz), 3.72 (2H, s), 6.95–7.33 (9H, m).

MS (APCI$^+$) 357 (M+1).

REFERENCE EXAMPLE 14

N-[3-(4-Benzyl-1-piperidinyl)propyl]-4-methylbenzylamine

Using 4-methylbenzylamine, the title compound was synthesized in a manner similar to Reference Example 7.

$^1$H NMR (CDCl$_3$) δ 1.33 (2H, dt, J=12.2 Hz, 2.6 Hz), 1.52 (1H, m), 1.56–1.84 (6H, m), 2.25 (3H, s), 2.39 (2H, t, J=7.6 Hz), 2.52 (2H, d, J=6.8 Hz), 2.70 (2H, t, J=7.0 Hz), 2.90 (2H, d, J=11.8 Hz), 3.78 (2H, s), 7.15–7.35 (9H, m).

MS (APCI$^+$) 337 (M+1).

REFERENCE EXAMPLE 15

N-[3-(4-Benzyl-1-piperidinyl)propyl]-4-methoxybenzylamine

Using 4-methoxybenzylamine, the title compound was synthesized in a manner similar to Reference Example 7.

$^1$H NMR (CDCl$_3$) δ 1.33 (2H, dt, J=12.2 Hz, 2.6 Hz), 1.52 (1H, m), 1.56–1.91 (6H, m), 2.39 (2H, t, J=7.8 Hz), 2.48 (2H, d, J=6.8 Hz), 2.69 (2H, t, J=6.8 Hz), 2.91 (2H, d, J=11.8 Hz), 3.80 (2H, s), 3.94 (3H, s), 7.12–7.47 (9H, m).

MS (APCI$^+$) 353 (M+1).

REFERENCE EXAMPLE 16

N-[3-(4-Benzyl-1-piperidinyl)propyl](cyclohexylmethyl)amine

Using (cyclohexylmethyl)amine, the title compound was synthesized in a manner similar to Reference Example 7.

$^1$H NMR (CDCl$_3$) δ 0.90 (2H, t, J=10.4 Hz), 1.17–1.30 (7H, m), 1.53–1.94 (11H, m), 2.35 (2H, t, J=7.8 Hz), 2.50–2.53 (4H, m), 2.66 (2H, t, J=6.8 Hz), 2.90 (2H, d, J=11.8 Hz), 7.09–7.21 (5H, m).

MS (APCI$^+$) 329 (M+1).

REFERENCE EXAMPLE 17

N-[3-(4-Benzyl-1-piperidinyl)propyl](3-pyridylmethyl)amine

Using 3-(aminomethyl)pyridine, the title compound was synthesized in a manner similar to Reference Example 7.

$^1$H NMR (CDCl$_3$) δ 1.30 (2H, dt, J=11.8 Hz, 2.4 Hz), 1.49 (1H, m), 1.51–1.95 (6H, m), 2.39 (2H, t, J=7.8 Hz), 2.54 (2H, d, J=7.2 Hz), 2.69 (2H, t, J=7.0 Hz), 2.92 (2H, d, J=12.2 Hz), 3.79 (2H, s), 7.15–7.19 (7H, m), 8.25 (1H, d, J=2.0 Hz), 8.54 (1H, d, J=1.8 Hz).

MS (APCI$^+$) 324 (M+1).

REFERENCE EXAMPLE 18-1

4-{[1-(Trifluoroacetyl)-4-piperidinyl]methyl}benzenesulfonyl chloride

To the mixture of 1-(trifluoroacetyl)-4-benzylpiperidine (29.2 g, 108 mmol) and methylene chloride (10 ml) was dropwise added chlorosulfonic acid (36 ml, 539 mmol) at −10° C. for an hour. The mixture was stirred at 0° C. for an hour and then stirred at room temperature for an hour. The reaction mixture was poured into ice-cooled water (500 ml) and extracted with methylene chloride (200 ml×2). The extract was washed with an aqueous solution of 5% sodium bicarbonate (500 ml) and saturated brine (500 ml) successively. The organic phase was dried over magnesium sulfate (anhydrous), then concentrated under reduced pressure. The residue was purified by flash column chromatography (silica gel 100 g, ethyl acetate/hexane=1/20→1/5) to give the title compound as a colorless powdery crystal (16.5 g, 41%).

$^1$H NMR (CDCl$_3$) δ 1.26–1.39 (2H, m), 1.75–2.05 (3H, m), 2.66–2.78 (1H, m), 2.48 (2H, d, J=7.0 Hz), 3.01–3.15 (1H, m), 3.98–4.10 (1H, m), 4.50–4.61 (1H, m), 7.40 (2H, d, J=8.4 Hz), 7.98 (2H, d, J=8.4 Hz).

REFERENCE EXAMPLE 18-2

4-[(4-{[1-(Trifluoroacetyl)-4-piperidinyl]methyl}phenyl)sulfonyl]morpholine

Morpholine (0.88 ml, 10.1 mmol) was added to a solution of the compound obtained in Reference Example 18-1 (1.5 g, 4.1 mmol) in THF (10 ml) at 0° C. The mixture was stirred for an hour. The obtained reaction solution was diluted by 1N hydrochloric acid, and extracted with ethyl acetate (50 ml). The organic phase was washed with saturated brine (50 ml) and dried over sodium sulfate (anhydrous). The solvent was removed under reduced pressure. The residue was purified by flash column chromatography to give (silica gel 20 g, ethyl acetate/hexane=1/5→1/1) the title compound (1.37 g, 80%) as a pale yellow oil.

$^1$H NMR (CDCl$_3$) δ 1.17–1.38 (2H, m), 1.73–1.94 (3H, m), 2.66 (2H, d, J=7.0 Hz), 2.68–2.78 (1H, m), 3.00 (4H, t, J=4.8 Hz), 3.01–3.15 (1H, m), 3.76 (4H, t, J=4.8 Hz), 3.98–4.10 (1H, m), 4.53–4.60 (1H, m), 7.33 (2H, d, J=8.4 Hz), 7.69 (2H, d, J=8.4 Hz).

REFERENCE EXAMPLE 18-3

4-{[4-(4-Piperidinylmethyl)phenyl]sulfonyl}morpholine

The mixture of the compound obtained in Reference Example 18-2 (1.3 g, 3 mmol), an aqueous solution of 1M potassium carbonate (10 ml) and methanol (20 ml) was stirred at room temperature for 5 hours. Saturated brine (20 ml) was added to the mixture, and the mixture was extracted with methylene chloride (20 ml→2) and diethyl ether (20 ml) successively. The extract was dried over magnesium sulfate (anhydrous). The solvent was removed under reduced pressure to give the title compound as a colorless powdery crystal (937 mg, 48%).

$^1$H NMR (CDCl$_3$) δ 1.21–1.82 (5H, m), 2.60–2.71 (4H, m), 3.00 (4H, t, J=4.8 Hz), 3.19–3.26 (2H, m), 3.75 (4H, t, J=4.8 Hz), 5.08 (1H, brs), 7.32 (2H, d, J=8.4 Hz), 7.67 (2H, d, J=8.4 Hz).

REFERENCE EXAMPLE 18-4

N-(3-{4-[4-(4-Morpholinylsulfonyl)benzyl]-1-piperidinyl}propyl)aniline dihydrochloride Using the compound obtained in Reference Example 18-3, the title compound was obtained in a manner similar to Reference Example 1. Yield 30%.

Free base: $^1$H NMR (CDCl$_3$) δ 1.23–2.10 (9H, m), 2.47 (2H, t, J=6.4 Hz), 2.64 (2H, t, J=6.4 Hz), 2.89–3.06 (6H, m), 3.17 (2H, t, J=6.4 Hz), 3.68–3.80 (4H, m), 6.57–6.72 (3H, m), 7.14–7.22 (2H, m), 7.33 (2H, d, J=8.2 Hz), 7.67 (2H, d, J=8.2 Hz).

REFERENCE EXAMPLE 19-1

4-[(1-Acetyl-4-piperidinyl)methyl]benzenesulfonyl chloride

To chlorosulfonic acid (92 mL), a solution of 1-acetyl-4-benzylpiperidine (60.00 g) in dichloromethane (100 mL) was dropwise added for an hour at 0° C. under stirring, and the mixture was stirred at 0° C. for 30 minutes and at room temperature for 1.5 hours. The reaction mixture was poured into ice-cooled water (1 L) and extracted with dichloromethane (500 mL, 250 mL). The organic phase was washed with an aqueous solution of 5% sodium carbonate (500 mL×2) and saturated brine (250 mL). The organic phase was dried over magnesium sulfate (anhydrous), and concentrated under reduced pressure. The residue was subjected to column chromatography (silica gel 250 g, ethyl acetate). The objective fraction was concentrated under reduced pressure to give the title compound as a white solid (54.22 g).

$^1$H NMR (CDCl$_3$) δ 1.05–1.35 (2H, m), 1.6–1.95 (3H, m), 2.09 (3H, s), 2.35–2.65 (1H, m), 2.68 (2H, d, J=6.6 Hz), 2.85–3.15 (1H, m), 3.7–3.9 (1H, m), 4.5–4.75 (1H, m), 7.39 (2H, d, J=8.4 Hz), 7.97 (2H, d, J=8.4 Hz).

REFERENCE EXAMPLE 19-2

1-Acetyl-4-[4-(methylsulfonyl)benzyl]piperidine

To a solution of sodium hydrogensulfite (4.57 g) and sodium bicarbonate (6.10 g) in water (40 mL) was added 4-[(1-acetyl-4-piperidinyl)methyl]benzenesulfonyl chloride (11.46 g) at 75° C. under stirring, and the mixture was stirred at 75° C. for an hour. Chloroacetic acid (5.14 g) and an aqueous solution of 50% sodium hydroxide (4.4 mL) was added to the reaction solution and stirred for 20 hours under reflux with heat. 1N Hydrochloric acid (20 ml) was added to the reaction mixture at 0° C., and the reaction mixture was extracted with ethyl acetate (60 mL, 30 mL). The organic phase was washed with saturated brine (10 mL×2), dried over magnesium sulfate (anhydrous), and concentrated under reduced pressure. The residue was subjected to column chromatography (silica gel 150 g, ethyl acetate/methanol=1/0→9/1). The objective fraction was concentrated under reduced pressure to give the title compound as a colorless oil (8.76 g).

$^1$H NMR (CDCl$_3$) δ 1.05–1.35 (2H, m), 1.55–1.95 (3H, m), 2.08 (3H, s), 2.4–2.6 (1H, m), 2.66 (2H, d, J=7.4 Hz), 2.9–3.1 (1H, m), 3.06 (3H, s), 3.7–3.9 (1H, m), 4.55–4.7 (1H, m), 7.34 (2H, d, J=8.4 Hz), 7.87 (2H, d, J=8.4 Hz).

REFERENCE EXAMPLE 19-3

4-[4-(Methylsulfonyl)benzyl]piperidine hydrochloride

A mixture of 1-acetyl-4-[4-(methylsulfonyl)benzyl]-piperidine (8.76 g) and concentrated hydrochloric acid (100 mL) was stirred for 4 hours under reflux with heat. The reaction mixture was concentrated under reduced pressure. 2-Propanol (100 mL) was added thereto and the mixture was concentrated under reduced pressure. To the residue was added 2-propanol (50 mL), and the mixture was stirred under reflux with heat for 30 minutes and cooled down to room temperature. The precipitate was filtered off, washed with 2-propanol (50 mL) and dried under reduced pressure to give the title compound as a white solid (7.51 g).

$^1$H NMR (CD$_3$OD) δ 1.3–1.6 (2H, m), 1.75–2.1 (3H, m), 2.75 (2H, d, J=7.0 Hz), 2.8–3.05 (2H, m), 3.10 (3H, s), 3.25–3.45 (2H, m), 7.49 (2H, d, J=8.1 Hz), 7.89 (2H, d, J=8.1 Hz).

REFERENCE EXAMPLE 19-4

4-[4-(Methylsulfonyl)benzyl]piperidine

4-[4-(Methylsulfonyl)benzyl]piperidine hydrochloride (1000 mg) was dissolved in water (10 mL). An aqueous solution of 1N sodium hydroxide (5 mL) was added to the solution at 0° C., and the aqueous phase was extracted with dichloromethane (10 mL×3). The organic phase was dried over potassium carbonate and filtered, and the filtrate was concentrated under reduced pressure. Diisopropyl ether (10 mL) was added to the residue, and the precipitate was collected by filtration. The precipitate was washed with diisopropyl ether and dried under reduced pressure to give the title compound as a white solid (712 mg).

$^1$H NMR (CDCl$_3$) δ 1.07–1.27 (2H, m), 1.50–1.73 (3H, m), 2.48–2.61 (2H, m), 2.62 (2H, d, J=6.6 Hz), 3.03–3.08 (2H, m), 3.05 (3H, s), 7.34 (2H, d, J=8.4 Hz), 7.85 (2H, d, J=8.4 Hz).

REFERENCE EXAMPLE 19-5

N-(3-{4-[4-(4-Methylsulfonyl)benzyl]-1-piperidinyl}propyl)aniline dihydrochloride Using 4-[4-(methylsulfonyl)benzyl]piperidine, the title compound was synthesized in a manner similar to Reference Example 1. Yield 30%.

$^1$H NMR (CD$_3$OD) δ 1.59–2.35 (7H, m), 2.75 (2H, d, J=6.4 Hz), 2.86–3.05 (2H, m), 3.13 (3H, s), 3.22 (2H, t, J=7.4 Hz), 3.48 (2H, t, J=8.0 Hz), 3.59–3.68 (2H, m), 6.63–6.75 (3H, m), 7.10–7.25 (2H, m), 7.50 (2H, d, J=8.2 Hz), 7.90 (2H, d, J=8.2 Hz).

REFERENCE EXAMPLE 20

N-[3-(4-Benzyl-1-piperidinyl)propyl]-4-cyanoaniline

Using 4-cyanoaniline, the title compound was synthesized in a manner similar to Reference Example 1.

$^1$H NMR (CDCl$_3$) δ 1.19–1.39 (2H, m), 1.45–1.96 (7H, m), 2.42–2.49 and 2.56–2.60 (2H and 2H, m), 2.90–2.97 and 3.15–3.24 (2H and 2H, m), 6.17–6.30 (1H, br s), 6.45 (2H, d, J=9.0 Hz), 7.14–7.42 (7H, m).

REFERENCE EXAMPLE 21

N-[3-(4-Benzyl-1-piperidinyl)propyl]-3-cyanoaniline

Using 3-cyanoaniline, the title compound was synthesized in a manner similar to Reference Example 1.

$^1$H NMR (CDCl$_3$) δ 1.20–1.40 (2H, m), 1.41–1.95 (7H, m), 2.42–2.49 and 2.56–2.60 (2H and 2H, m), 2.91–2.98 and 3.11–3.19 (2H and 2H, m), 6.68–6.74 (2H, m), 6.89–6.93 (1H, m), 7.14–7.30 (6H, m).

REFERENCE EXAMPLE 22

N-[3-(4-Benzyl-1-piperidinyl)propyl]-3-pyridineamine

Using 3-aminopyridine, the title compound was synthesized in a manner similar to Reference Example 1. Yield 38%.

$^1$H NMR (CDCl$_3$) δ 1.17–1.93 (9H, m), 2.45 (2H, t, J=6.6 Hz), 2.56 (2H, d, J=6.6 Hz), 2.93 (2H, m), 3.17 (2H, t, J=6.2 Hz), 5.20 (1H, bs), 6.81 (1H, m), 7.03–7.33 (6H, m), 7.91 (1H, dd, J=1.2 Hz, 4.8 Hz), 7.99 (1H, d, J=2.6 Hz).

REFERENCE EXAMPLE 23-1 tert-Butyl 4-(4-methoxycarbonylbenzyl)piperidine-1-carboxylate

The mixture of methyl 4-(bromomethyl)benzoate (25 g, 109 mmol and triethyl phosphite (24.3 ml, 142 mmol) was stirred at 150° C. for 24 hours. The reaction mixture was distilled under reduced pressure (165–172° C., 1 mmHg) to give diethyl 4-(methylcarbonyl)benzyl phosphonate (21.5 g, 69%).

Sodium hydride (60% oily, 2.9 g, 71.5 mmol) was added to a solution of diethyl 4-(methylcarbonyl)benzyl phosphonate (20.5 g, 71.5 mmol) and 15-crown 5 (1.4 ml, 7.1 mmol) in THF (120 ml) at 0° C. and the mixture was stirred for 0.5 hour at the same temperature. A solution of tert-butyl 4-oxo-1-piperidinecarboxylate (11.9 g, 59.6 mmol) in THF (45 ml) was dropwise added to the mixture at 0° C. for 10 minutes, and the mixture was stirred at room temperature for 20 hours. The reaction mixture was poured into an ice-water (200 ml) and the mixture was extracted with ethyl acetate (100 ml×2). The extract was washed with 5% sodium bicarbonate (100 ml) and saturated brine (100 ml) successively, dried over sodium sulfate (anhydrous) and concentrated under reduced pressure. The residue was purified by flash column chromatography (silica gel 200 g, ethyl acetate/hexane=1/10) to give tert-butyl 4-(4-methoxycarbonylbenzylidene)piperidine-1-carboxylate (6.9 g, 35%) as a colorless powdery crystal.

A solution of tert-butyl 4-(4-methoxycarbonylbenzylidene)piperidine-1-carboxylate (6 g, 18 mmol) in methanol (150 ml) was subjected to catalytic hydrogenation in the presence of 10% palladium-carbon (containing 50% water, 1 g) at room temperature for 5 hours. The catalyst was filtered off, and the filtrate was condensed under reduced pressure. The residue was purified by flash column chromatography (silica gel 90 g, ethyl acetate/hexane=1/10) to give the title compound as a pale yellow oil (6.1 g, 100%).

$^1$H NMR (CDCl$_3$) δ 1.05–1.42 (2H, m), 1.45 (9H, s), 1.55–1.77 (3H, m), 2.59 (2H, d, J=7.0 Hz), 2.57–2.69 (2H, m), 3.91 (3H, s), 4.04–4.18 (2H, m), 7.21 (2H, d, J=8.0 Hz), 7.96 (2H, d, J=8.0 Hz).

REFERENCE EXAMPLE 23-2

4-{[1-(tert-Butoxycarbonyl)-4-piperidinyl]methyl}benzoic acid

A mixture of the compound obtained in Reference Example 23-1 (3 g, 9 mmol), ethanol (30 ml) and an aqueous solution of 1N sodium hydroxide (14 ml) was stirred at 80° C. for 5 hours. The obtained reaction mixture was concentrated under reduced pressure. The residue was purified by flash column chromatography (silica gel 100 g, ethyl acetate/methanol=10/1) to give the title compound as a white powdery crystal (2.9 g, 9%).

$^1$H NMR (CDCl$_3$) δ 1.08–1.26 (2H, m), 1.45 (9H, s), 1.57–1.77 (3H, m), 1.26–2.70 (2H, m), 2.61 (2H, d, J=7.4 Hz), 4.05–4.11 (2H, m), 7.24 (2H, d, J=8.0 Hz), 8.03 (2H, d, J=8.0 Hz).

REFERENCE EXAMPLE 23-3 tert-Butyl 4-[4-(aminocarbonyl)benzyl]-1-piperidinecarboxylate

Hydroxy-1H-benzotriazole (3.6 g, 27 mmol), ammonium chloride (1.9 g, 35.1 mmol), triethylamine (4.9 ml, 35.1 ml) and 1-ethyl-3-(3-dimethylaminopropyl)carbodiimide hydrochloride (6.7 g, 35.1 mmol) were added to a solution of the compound obtained in Reference Example 23-2 (8.6 g, 22.7 mmol) in DMF (160 ml) at 0° C. and the mixture was stirred at room temperature for 20 hours. The reaction mixture was concentrated under reduced pressure. Water (200 ml) was added to the residue, and the mixture was extracted with ethyl acetate (200 ml×2). The extract was washed with 0.5N hydrochloric acid (200 ml), 5% sodium bicarbonate (200 ml) and saturated brine (100 ml) successively, dried over sodium sulfate (anhydrous) and concentrated under reduced pressure. The residue was purified by flash column chromatography (silica gel 200 g, ethyl acetate/hexane=1/1→3/1) and recrystallized from hexane to give the title compound as a colorless powdery crystal (8.1 g, 94%).

$^1$H NMR (CDCl$_3$) δ 1.05–1.25 (2H, m), 1.45 (9H, s), 1.56–1.76 (3H, m), 2.59 (2H, d, J=2.0 Hz), 2.57–2.69 (2H, m), 4.04–4.10 (2H, m), 5.50–6.20 (2H, br), 7.22 (2H, d, J=8.4 Hz), 7.74 (2H, d, J=8.4 Hz).

REFERENCE EXAMPLE 23-4

4-(4-Piperidinylmethyl)benzamide hydrochloride

A solution of 4N hydrogen chloride in ethyl acetate (120 ml) was added to a solution of the compound obtained in Reference Example 23-3 (8.1 g, 25.4 mmol) in methanol (120 ml), and the mixture was stirred at room temperature for 3 hours. The obtained solution was concentrated under reduced pressure. The residue was crystallized from diisopropyl ether-ethyl acetate (1/1, 20 ml) to give the title compound as a colorless powdery crystal (5.97 g, 73%).

$^1$H NMR (CD$_3$OD) δ 1.25–1.56 (2H, m), 1.82–2.01 (3H, m), 2.68 (2H, d, J=6.8 Hz), 2.88–3.01 (2H, m), 3.30–3.40 (2H, m), 7.31 (2H, d, J=8.4 Hz), 7.82 (2H, d, J=8.4 Hz).

REFERENCE EXAMPLE 23-5

4-(4-Piperidinylmethyl)benzamide

The compound obtained in Reference Example 23-4 (10 g, 39.3 mmol) was added to an aqueous solution of 1N sodium hydroxide (86 ml) at 0° C., and the mixture was stirred at room temperature for an hour. The resulting precipitate was collected by filtration to give the title compound as a colorless powdery crystal (5.96 g, 70%).

$^1$H NMR (CDCl$_3$) δ 1.07–1.30 (2H, m), 1.58–1.75 (4H, m), 2.48–2.60 (4H, m), 3.01–3.07 (2H, m), 5.70–6.40 (2H, br), 7.23 (2H, d, J=7.4 Hz), 7.74 (2H, d, J=7.4 Hz).

REFERENCE EXAMPLE 23-6

4-{[1-(3-Anilinopropyl)-4-piperidinyl]methyl}benzamide hydrochloride

Using the compound obtained in Reference Example 23-5 and aniline, the title compound was synthesized in a manner similar to Reference Example 1. Yield 20%.

$^1$H NMR (CD$_3$OD) δ 1.49–1.68 (2H, m), 1.80–2.01 (3H, m), 2.15–2.30 (2H, m), 2.69 (2H, d, J=Hz), 2.89–3.01 (2H, m), 3.17–3.25 (2H, m), 3.46–3.60 (4H, m), 7.31 (2H, d, J=8.0 Hz) 7.43–7.61 (5H, m), 7.82 (2H, d, J=8.0 Hz).

EXAMPLE 1

N-[3-(4-Benzyl-1-piperidinyl)propyl]-N-phenyl-N'-phenylurea hydrochloride

To a solution of phenyl isocyanate (163 μl, 1.5 mmol) in THF (15 ml) were added the compound obtained in Reference Example 1 (381 mg, 1.0 mmol) and a solution of triethylamine (308 μl, 2.2 mmol) in dichloromethane (15 ml) at room temperature for an hour under stirring. The mixture was stirred for 12 hours at room temperature. Dichloromethane (50 ml) was added to the mixture, then the mixture was washed with saturated aqueous solution of sodium bicarbonate (50 ml×2). The organic phase was dried over with magnesium sulfate (anhydrous) and concentrated under reduced pressure. The residue was subjected to column chromatography (silica gel 12 g, hexane/ethyl acetate= 1/1→0/1). The objective fraction was concentrated under reduced pressure. The residue was dissolved in ethyl acetate (2 ml), and a solution of 4N hydrogen chloride in ethyl acetate (2 ml) was added thereto. The mixture was stirred for 5 minutes and concentrated under reduced pressure. Hexane (5 ml) was added to the residue, and the precipitate was collected by filtration and dried under reduced pressure to give the title compound as a white amorphous. Yield 82%.

$^1$H NMR (DMSO-d$_6$) δ 1.30–1.95 (7H, m), 2.54–2.57 (2H, m), 2.80–2.93 (2H, m), 3.00–3.12 (2H, m), 3.42–3.80 (2H, m), 3.62–3.78 (2H, m), 6.95–7.55 (15H, m), 7.85 (1H, s).

Anal. Calcd for C$_{28}$H$_{33}$N$_3$O.HCl.0.75H$_2$O: C, 70.42; H, 7.71; N, 8.80. Found: C, 70.43; H, 7.31; N, 8.74.

EXAMPLE 2

N-[3-(4-Benzyl-1-piperidinyl)propyl]-N'-(4-chlorophenyl)-N-phenylurea

To a solution of the compound obtained in Reference Example 1 (22.9 g, 60 mmol) and triethylamine (18.5 ml, 132 mmol) in dichloromethane (500 ml) was added 4-chlorophenyl isocyanate (13.8 g, 90 mmol) under stirring, and the mixture was stirred at room temperature for 12 hours. The reaction mixture was washed with saturated sodium bicarbonate (400 ml×2), dried over magnesium sulfate (anhydrous) and concentrated under reduced pressure. The residue was subjected to column chromatography (silica gel 500 g, hexane/ethyl acetate=1/1→0/1). The objective fraction was concentrated under reduced pressure. The residue was recrystallized from diethyl ether (45 ml). The precipitate was filtered and collected. The precipitate was washed with diethyl ether and dried under reduced pressure to give the title compound as a white crystal (13.8 g, 30 mmol). Yield 50%.

Melting Point 101–103° C.

$^1$H NMR (CDCl$_3$) δ 1.23–1.46 (2H, m), 1.46–1.90 (7H, m), 2.36 (2H, t, J=7.3 Hz), 2.51 (2H, d, J=6.6 Hz), 2.82–2.90 (2H, m), 3.77 (2H, t, J=7.3 Hz), 6.66 (1H, br), 7.1–7.52 (14H, m).

Anal. Calcd. for C$_{28}$H$_{32}$ClN$_3$O: C, 72.79; H, 6.98; Cl, 7.67; N, 9.09. Found: C, 72.41; H, 6.97; Cl, 7.72; N, 8.98.

EXAMPLE 3

N-[3-(4-Benzyl-1-piperidinyl)propyl]-N'-(3-chlorophenyl)-N-phenylurea hydrochloride Using 3-chlorophenyl isocyanate, the title compound was obtained in a manner similar to Example 1. Yield 72%.

$^1$H NMR (DMSO-d$_6$) δ 1.45–1.86 (7H, m), 2.49–2.53 (2H, m), 2.77–2.89 (2H, m), 3.00–3.17 (2H, m), 3.35–3.40 (2H, m), 3.69–3.76 (2H, m), 6.94–6.70 (1H, m), 7.15–7.50 (12H, m), 7.60–7.64 (1H, m), 8.15 (1H, s).

Anal. Calcd for C$_{28}$H$_{32}$ClN$_3$O.HCl.1.0H$_2$O: C, 65.11; H, 6.83; N, 8.14. Found: C, 65.20; H, 6.69; N, 7.95.

EXAMPLE 4

N-[3-(4-Benzyl-1-piperidinyl)propyl]-N'-(4-methylphenyl)-N-phenylurea hydrochloride Using p-tolyl isocyanate, the title compound was obtained in a manner similar to Example 1. Yield 75%.

$^1$H NMR (DMSO-d$_6$) δ 1.45–1.91 (7H, m), 2.21 (3H, s), 2.49–2.53 (2H, m), 2.77–2.85 (2H, m), 3.00–3.18 (2H, m), 3.35–3.44 (2H, m), 3.68–3.76 (2H, m), 6.97–7.02 (2H, m), 7.15–7.50 (12H, m), 7.75 (1H, s).

Anal. Calcd for C$_{29}$H$_{35}$N$_3$O.HCl.0.75H$_2$O: C, 70.85; H, 7.69; N, 8.55. Found: C, 70.85; H, 7.67; N, 8.42.

EXAMPLE 5

N'-Benzyl-N-[3-(4-benzyl-1-piperidinyl)propyl]-N-phenylurea hydrochloride

Using benzyl isocyanate, the title compound was obtained in a manner similar to Example 1. Yield 67%.

$^1$H NMR (DMSO-d$_6$) δ 1.40–1.81 (7H, m), 2.53–2.56 (2H, m), 2.77–2.89 (2H, m), 2.98–3.18 (2H, m), 3.35–3.40 (2H, m), 3.65–3.70 (2H, m), 4.20 (2H, s), 7.18–7.54 (15H, m).

Anal. Calcd. for C$_{29}$H$_{35}$N$_3$O.HCl.0.5H$_2$O: C, 71.51; H, 7.66; N, 8.63. Found: C, 71.60; H, 7.74; N, 8.46.

EXAMPLE 6

N-[3-(4-Benzyl-1-piperidinyl)propyl]-N'-cyclohexyl-N-phenylurea

Using cyclohexyl isocyanate, the title compound was obtained in a manner similar to Example 2. Yield 72%.

Melting Point 106–108° C.

$^1$H NMR (CDCl$_3$) δ 0.8–1.95 (19H, m), 2.30 (2H, t, J=7.6 Hz), 2.50 (2H, d, J=6.6 Hz), 2.83 (2H, br d, J=11.8 Hz), 3.4–3.75 (1H, m), 3.68 (2H, t, J=7.3 Hz), 4.15 (1H, d, J=8.0 Hz), 7.05–7.5 (10H, m).

Anal. Calcd for $C_{28}H_{39}N_3O$: C, 77.55; H, 9.07; N, 9.69. Found: C, 77.65; H, 8.96; N, 9.75.

EXAMPLE 7

N-[3-(4-Benzyl-1-piperidinyl)propyl]-N-phenyl-N'-propylurea

Using propyl isocyanate, the title compound was obtained in a manner similar to Example 2. Yield 92%.

$^1$H NMR (CDCl$_3$) δ 0.84 (3H, t, J=7.3 Hz), 1.1–1.95 (11H, m), 2.33 (2H, t, J=7.6 Hz), 2.53 (2H, d, J=6.6 Hz), 2.86 (2H, br d, J=11.6 Hz), 3.05–3.2 (2H, m), 3.71 (2H, t, J=7.3 Hz), 4.55–4.7 (1H, m), 7.1–7.5 (10H, m).

EXAMPLE 8

N-[3-(4-Benzyl-1-piperidinyl)propyl]-N-(3-chlorophenyl)-N'-(4-chlorophenyl)urea hydrochloride Using the compound obtained in Reference Example 2, the title compound was obtained in a manner similar to Example 2.

Yield 27%.

$^1$H NMR (DMSO-d$_6$) δ 1.40–1.91 (7H, m), 2.51–2.54 (2H, m), 2.78–2.90 (2H, m), 3.00–3.17 (2H, m), 3.37–3.43 (2H, m), 3.71–3.78 (2H, m), 7.15–7.50 (13H, m), 8.34 (1H, s).

Anal. Calcd. for $C_{28}H_{31}Cl_2N_3O\cdot HCl\cdot 1.0H_2O$: C, 61.04; H, 6.22; N, 7.63. Found: C, 60.80; H, 6.20; N, 7.73.

EXAMPLE 9

N-[3-(4-Benzyl-1-piperidinyl)propyl]-N'-(4-chlorophenyl)-N-(3,4-dichlorophenyl)urea Using the compound obtained in Reference Example 3, the title compound was obtained in a manner similar to Example 2.

Yield 78%.

Melting Point 128–131° C.

$^1$H NMR (CDCl$_3$) δ 1.1–2.0 (9H, m), 2.39 (2H, t, J=6.8 Hz), 2.51 (2H, d, J=6.2 Hz), 2.88 (2H, br d, J=11.8 Hz), 3.78 (2H, t, J=6.6 Hz), 7.05–7.4 (10H, m), 7.41 (1H, d, J=2.6 Hz), 7.49 (1H, d, J=8.4 Hz), 7.90 (1H, br s).

EXAMPLE 10

N-[3-(4-Benzyl-1-piperidinyl)propyl]-N'-(4-chlorophenyl)-N-(4-methylphenyl)urea hydrochloride Using the compound obtained in Reference Example 4, the title compound was obtained in a manner similar to Example 2.

Yield 87%.

$^1$H NMR (DMSO-d$_6$) δ 1.2–1.95 (7H, m), 2.34 (3H, s), 2.45–2.6 (2H, m), 2.6–3.5 (6H, m), 3.68 (2H, t, J=6.8 Hz), 7.1–7.35 (11H, m), 7.44 (2H, d, J=9.2 Hz), 7.93 (1H, s).

Anal. Calcd. for $C_{29}H_{34}ClN_3O\cdot HCl\cdot 0.5H_2O$: C, 66.79; H, 6.96; Cl, 13.60; N, 8.06. Found: C, 66.84; H, 6.99; Cl, 13.51; N, 7.95.

EXAMPLE 11

N'-(4-Chlorophenyl)-N-{3-[4-(4-fluorobenzyl)-1-piperidinyl]-propyl}-N-phenylurea Using the compound obtained in Reference Example 5, the title compound was obtained in a manner similar to Example 2.

Yield 94%.

$^1$H NMR (CDCl$_3$) δ 1.1–2.0 (9H, m), 2.36 (2H, br t, J=7.3 Hz), 2.48 (2H, d, J=6.6 Hz), 2.86 (2H, br d, J=11.6 Hz), 3.77 (2H, t, J=7.1 Hz), 6.60 (1H, br s), 6.85–7.55 (13H, m).

EXAMPLE 12

N'-(4-Chlorophenyl)-N-(3,4-dichlorophenyl)-N-{3-[4-(4-fluorobenzyl)-1-piperidinyl]propyl}urea Using the compound obtained in Reference Example 6, the title compound was obtained in a manner similar to Example 2.

Yield 79%.

Melting Point 113–115° C.

$^1$H NMR (CDCl$_3$) δ 1.1–2.0 (9H, m), 2.40 (2H, br t, J=6.6 Hz), 2.48 (2H, d, J=6.6 Hz), 2.89 (2H, br d, J=11.4 Hz), 3.78 (2H, t, J=6.8 Hz), 6.9–7.4 (9H, m), 7.42 (1H, d, J=2.6 Hz), 7.50 (1H, d, J=8.8 Hz), 7.77 (1H, br s).

EXAMPLE 13

N-[3-(4-Benzyl-1-piperidinyl)propyl]-N'-(1-naphthyl)-N-phenylurea

Using 1-naphthyl isocyanate, the title compound was obtained in a manner similar to Example 2. Yield 74%.

Melting Point 124–127° C.

$^1$H NMR (CDCl$_3$) δ 1.0–1.95 (9H, m), 2.3–2.5 (2H, m), 2.39 (2H, d, J=6.6 Hz), 2.86 (2H, br d, J=11.4 Hz), 3.88 (2H, t, J=7.3 Hz), 7.0–7.3 (6H, m), 7.3–7.65 (10H, m), 7.75–7.85 (1H, m), 7.9–8.0 (1H, m).

Anal. Calcd for $C_{32}H_{35}N_3O$: C, 80.47; H, 7.39; N, 8.80. Found: C, 80.33; H, 7.21; N, 8.83.

EXAMPLE 14

N-Benzyl-N-[3-(4-benzyl-1-piperidinyl)propyl]-N'-(2,6-dimethylphenyl)urea trifluoroacetate Triethylamine (14 μl, 100 μmol) was added to a solution of the compound obtained in Reference Example 7 (16.1 mg, 50 μmol) in dichloromethane (0.3 ml) at room temperature. Then, a solution of 2,6-dimethylphenyl isocyanate (11.0 mg, 75 μmol) in dichloromethane (0.4 ml) was added thereto at room temperature, and the mixture was stirred for 24 hours. After the reaction was completed, the mixture was concentrated under reduced pressure. The residue was dissolved again in dichloromethane (0.5 ml). PS-trisamine resin (Argonaut, 3.62 mmol/g, 50 mg, 0.18 mmol) was added to the solution and the solution was stirred at room temperature for an hour. The resin was separated by filtration, and the filtrate was concentrated under reduced pressure. The residue was dissolved again in dichloromethane (0.5 ml). MP-carbonate resin (Argonaut, 2.64 mmol/g, 45 mg, 0.12 mmol) was added to the solution and stirred at room temperature for an hour. The resin was filtered off, and the filtrate was concentrated under reduced pressure and purified by preparative HPLC. The objective fraction was concentrated to give the title compound as a colorless oil (15.1 mg).

HPLC analysis (220 nm): purity 96% (Retention time 3.448 min).

MS (APCI$^+$) 470 (M+1).

EXAMPLE 15

N-Benzyl-N-[3-(4-benzyl-1-piperidinyl)propyl]-N'-(2-chlorophenyl)urea trifluoroacetate Using 2-chlorophenyl isocyanate, the title compound was synthesized in a manner similar to Example 14.

HPLC analysis (220 nm): purity 98% (Retention time 3.537 min).

MS (APCI$^+$) 476 (M+1).

EXAMPLE 16

N-Benzyl-N-[3-(4-benzyl-1-piperidinyl)propyl]-N'-(4-fluorophenyl)urea trifluoroacetate Using 4-chlorophenyl isocyanate, the title compound was synthesized in a manner similar to Example 14.

HPLC analysis (220 nm): purity 98% (Retention time 3.464 min).

MS (APCI$^+$) 460 (M+1).

EXAMPLE 17

N-Benzyl-N-[3-(4-benzyl-1-piperidinyl)propyl]-N'-(4-methylthiophenyl)urea trifluoroacetate Using 4-methylthiophenyl isocyanate, the title compound was synthesized in a manner similar to Example 14.

HPLC analysis (220 nm): purity 96% (Retention time 3.587 min).

MS (APCI$^+$) 488 (M+1).

EXAMPLE 18

N-Benzyl-N-[3-(4-benzyl-1-piperidinyl)propyl]-N'-(1-naphthyl)urea trifluoroacetate Using 1-naphthyl isocyanate, the title compound was synthesized in a manner similar to Example 14.

HPLC analysis (220 nm): purity 93% (Retention time 3.570 min).

MS (APCI$^+$) 492 (M+1).

EXAMPLE 19

N-Benzyl-N-[3-(4-benzyl-1-piperidinyl)propyl]-N'-(3-methylphenyl)urea trifluoroacetate Using 3-methylphenyl isocyanate, the title compound was synthesized in a manner similar to Example 14.

HPLC analysis (220 nm): purity 94% (Retention time 3.549 min).

MS (APCI$^+$) 456 (M+1).

EXAMPLE 20

N-Benzyl-N-[3-(4-benzyl-1-piperidinyl)propyl]-N'-(2,6-difluorophenyl)urea trifluoroacetate Using 2,6-difluorophenyl isocyanate, the title compound was synthesized in a manner similar to Example 14.

HPLC analysis (220 nm): purity 99% (Retention time 3.361 min).

MS (APCI$^+$) 478 (M+1).

EXAMPLE 21

N-Benzyl-N-[3-(4-benzyl-1-piperidinyl)propyl]-N'-(2,4-dimethoxyphenyl)urea trifluoroacetate Using 2,4-dimethoxyphenyl isocyanate, the title compound as synthesized in a manner similar to Example 14.

HPLC analysis (220 nm): purity 97% (Retention time 3.482 min).

MS (APCI$^+$) 502 (M+1).

EXAMPLE 22

N-Benzyl-N-[3-(4-benzyl-1-piperidinyl)propyl]-N'-[2-(trifluoromethyl)phenyl]urea trifluoroacetate Using 2-(trifluoromethyl)phenyl isocyanate, the title compound was synthesized in a manner similar to Example 14.

HPLC analysis (220 nm): purity 98% (Retention time 3.760 min).

MS (APCI$^+$) 510 (M+1).

EXAMPLE 23

N-Benzyl-N-[3-(4-benzyl-1-piperidinyl)propyl]-N'-(4-chlorophenyl)urea trifluoroacetate Using 4-chlorophenyl isocyanate, the title compound was synthesized in a manner similar to Example 14.

HPLC analysis (220 nm): purity 93% (Retention time 3.551 min).

MS (APCI$^+$) 476 (M+1).

EXAMPLE 24

N-Benzyl-N-[3-(4-benzyl-1-piperidinyl)propyl]-N'-(3,4-dichlorophenyl)urea trifluoroacetate Using 3,4-dichlorophenyl isocyanate, the title compound was synthesized in a manner similar to Example 14.

HPLC analysis (220 nm): purity 96% (Retention time 3.613 min).

MS (APCI$^+$) 510 (M+1).

EXAMPLE 25

N-Benzyl-N-[3-(4-benzyl-1-piperidinyl)propyl]-N'-(4-isopropylphenyl)urea trifluoroacetate Using 4-isopropylphenyl isocyanate, the title compound was synthesized in a manner similar to Example 14.

HPLC analysis (220 nm): purity 95% (Retention time 3.764 min).

MS (APCI$^+$) 484 (M+1).

EXAMPLE 26

N-Benzyl-N-[3-(4-benzyl-1-piperidinyl)propyl]-N'-(4-nitrophenyl)urea trifluoroacetate Using 4-nitrophenyl isocyanate, the title compound was synthesized in a manner similar to Example 14.

HPLC analysis (220 nm): purity 92% (Retention time 3.775 min).

MS (APCI$^+$) 487 (M+1).

EXAMPLE 27

N-Benzyl-N-[3-(4-benzyl-1-piperidinyl)propyl]-N'-(4-bromophenyl)urea trifluoroacetate Using 4-bromophenyl isocyanate, the title compound was synthesized in a manner similar to Example 14.

HPLC analysis (220 nm): purity 93% (Retention time 3.485 min).

MS (APCI$^+$) 520 (M+1).

EXAMPLE 28

N-Benzyl-N-[3-(4-benzyl-1-piperidinyl)propyl]-N'-(4-methoxyphenyl)urea trifluoroacetate Using 4-methoxyphenyl isocyanate, the title compound was synthesized in a manner similar to Example 14.

HPLC analysis (220 nm): purity 97% (Retention time 3.405 min).

MS (APCI+) 472 (M+1).

EXAMPLE 29

N-Benzyl-N-[3-(4-benzyl-1-piperidinyl)propyl]-N'-[2-(trifluoromethoxy)phenyl]urea trifluoroacetate Using 2-(trifluoromethoxy)phenyl isocyanate, the title compound was synthesized in a manner similar to Example 14.

HPLC analysis (220 nm): purity 100% (Retention time 3.637 min).

MS (APCI+) 526 (M+1).

EXAMPLE 30

N-[3-(4-Benzyl-1-piperidinyl)propyl]-N'-(4-chlorophenyl)-N-(4-fluorobenzyl)urea trifluoroacetate Triethylamine (14 µl, 100 µmol) was added to a solution of the compound obtained in Reference Example 8 (16.1 mg, 50 µmol) in dichloromethane (0.3 ml) at room temperature. Then, a solution of 4-chlorophenyl isocyanate (11.5 mg, 75 µmol) in dichloromethane (0.4 ml) was added to the solution at room temperature and the mixture was stirred for 24 hours. After the reaction was completed, the reaction mixture was concentrated under reduced pressure. The residue was dissolved again in dichloromethane (0.5 ml). PS-Tris amine resin (Argonaut, 3.62 mmol/g, 50 mg, 0.18 mmol) was added to the solution and the mixture was stirred at room temperature for an hour. The resin was filtered off, and the filtrate was concentrated under reduced pressure and dissolved again in dichloromethane (0.5 ml). MP-carbonate resin (Argonaut, 2.64 mmol/g, 45 mg, 0.12 mmol) was added to the solution and the mixture was stirred at room temperature for an hour. The resin was filtered off, and the filtrate was concentrated under reduced pressure and purified by preparative HPLC. The objective fraction was concentrated to give the title compound as a colorless oil (13.9 mg).

HPLC analysis (220 nm): purity 99% (Retention time 3.564 min).

MS (APCI+) 494 (M+1).

EXAMPLE 31

N-[3-(4-Benzyl-1-piperidinyl)propyl]-N-(3-chlorobenzyl)-N'-(4-chlorophenyl)urea trifluoroacetate Using the compound obtained in Reference Example 9, the title compound was synthesized in a manner similar to Example 30.

HPLC analysis (220 nm): purity 94% (Retention time 3.582 min).

MS (APCI+) 510 (M+1).

EXAMPLE 32

N-[3-(4-Benzyl-1-piperidinyl)propyl]-N'-(4-chlorophenyl)-N-(3,4-dichlorobenzyl)urea trifluoroacetate Using the compound obtained in Reference Example 10, the title compound was synthesized in a manner similar to Example 30.

HPLC analysis (220 nm): purity 93% (Retention time 3.637 min).

MS (APCI+) 544 (M+1).

EXAMPLE 33

N-[3-(4-Benzyl-1-piperidinyl)propyl]-N-(4-fluorobenzyl)-N'-(4-methoxyphenyl)urea trifluoroacetate Triethylamine (14 µl, 100 µmol) was added to a solution of the compound obtained in Reference Example 8 (16.1 mg, 50 µmol) in dichloromethane (0.3 ml) at room temperature. Then, a solution of 4-methoxyphenyl isocyanate (11.2 mg, 75 µmol) in dichloromethane (0.4 ml) was added to the solution at room temperature and the mixture was stirred for 24 hours. After the reaction was completed, the reaction solution was concentrated under reduced pressure and dissolved again in dichloromethane (0.5 ml). PS-TRIS amine resin (Argonaut, 3.62 mmol/g, 50 mg, 0.18 mmol) was added to the solution and stirred at room temperature for an hour. The resin was filtered off and the filtrate was concentrated under reduced pressure. The residue was dissolved again in dichloromethane (0.5 ml). MP-carbonate resin (Argonaut, 2.64 mmol/g, 45 mg, 0.12 mmol) was added to the solution and stirred at room temperature for an hour. The resin was filtered off, and the filtrate was concentrated under reduced pressure and purified by preparative HPLC. The objective fraction was concentrated to give the title compound as a colorless oil (12.6 mg).

HPLC analysis (220 nm): purity 96% (Retention time 3.471 min).

MS (APCI+) 490 (M+1).

EXAMPLE 34

N-[3-(4-Benzyl-1-piperidinyl)propyl]-N-(3-chlorobenzyl)-N'-(4-methoxyphenyl)urea trifluoroacetate Using the compound obtained in Reference Example 9, the title compound was synthesized in a manner similar to Example 33.

HPLC analysis (220 nm): purity 99% (Retention time 3.483 min).

MS (APCI+) 506 (M+1).

EXAMPLE 35

N-[3-(4-Benzyl-1-piperidinyl)propyl]-N-(3,4-dichlorobenzyl)-N'-(4-methoxyphenyl)urea trifluoroacetate Using the compound obtained in Reference Example 10, the title compound was synthesized in a manner similar to Example 33.

HPLC analysis (220 nm): purity 97% (Retention time 3.521 min).

MS (APCI+) 540 (M+1).

EXAMPLE 36

N-[3-(4-Benzyl-1-piperidinyl)propyl]-N'-cyclohexyl-N-(4-fluorobenzyl)urea trifluoroacetate Triethylamine (14 µl, 100 µmol) was added to a solution of the compound obtained in Reference Example 8 (16.1 mg, 50 µmol) in dichloromethane (0.3 ml) at room temperature. Then, a solution of cyclohexyl isocyanate (9.4 mg, 75 μmol) in dichloromethane (0.4 ml) was added to the mixture at room temperature, and the mixture was stirred for 24 hours. After the reaction was completed, the reaction mixture was concentrated under reduced pressure and dissolved again in dichloromethane (0.5 ml). PS-TRIS amine resin (Argonaut, 3.62 mmol/g, 50 mg, 0.18 mmol) was added to the solution and stirred at room temperature for an hour. The resin was filtered off, and the filtrate was concentrated under reduced pressure. The residue was dissolved again in dichloromethane (0.5 ml). MP-carbonate resin (Argonaut, 2.64 mmol/g, 45 mg, 0.12 mmol) was added to the solution and stirred at room temperature for an hour. The resin was filtered off, and the filtrate was concentrated under reduced pressure and purified by preparative HPLC. The objective fraction was concentrated to give the title compound as a colorless oil (12.2 mg).

HPLC analysis (220 nm): purity 100% (Retention time 3.500 min).

MS (APCI$^+$) 466 (M+1).

EXAMPLE 37

N-[3-(4-Benzyl-1-piperidinyl)propyl]-N-(3-chlorobenzyl)-N'-cyclohexylurea trifluoroacetate Using the compound obtained in Reference Example 9, the title compound was synthesized in a manner similar to Example 36.

HPLC analysis (220 nm): purity 100% (Retention time 3.579 min).

MS (APCI$^+$) 482 (M+1).

EXAMPLE 38

N-[3-(4-Benzyl-1-piperidinyl)propyl]-N'-cyclohexyl-N-(3,4-dichlorobenzyl)urea trifluoroacetate Using the compound obtained in Reference Example 10, the title compound was synthesized in a manner similar to Example 36.

HPLC analysis (220 nm): purity 99% (Retention time 3.753 min).

MS (APCI$^+$) 516 (M+1).

EXAMPLE 39

N-[3-(4-Benzyl-1-piperidinyl)propyl]-N'-(4-chlorophenyl)-N-(2,6-difluorobenzyl)urea trifluoroacetate Using the compound obtained in Reference Example 11, the title compound was synthesized in a manner similar to Example 30.

HPLC analysis (220 nm): purity 98% (Retention time 3.623 min).

MS (APCI$^+$) 512 (M+1).

EXAMPLE 40

N-[3-(4-Benzyl-1-piperidinyl)propyl]-N-(2-chlorobenzyl)-N'-(4-chlorophenyl)urea trifluoroacetate Using the compound obtained in Reference Example 12, the title compound was synthesized in a manner similar to Example 30.

HPLC analysis (220 nm): purity 100% (Retention time 3.588 min).

MS (APCI$^+$) 510 (M+1).

EXAMPLE 41

N-[3-(4-Benzyl-1-piperidinyl)propyl]-N-(4-chlorobenzyl)-N'-(4-chlorophenyl)urea trifluoroacetate Using the compound obtained in Reference Example 13, the title compound was synthesized in a manner similar to Example 30.

HPLC analysis (220 nm): purity 99% (Retention time 3.595 min).

MS (APCI$^+$) 510 (M+1).

EXAMPLE 42

N-[3-(4-Benzyl-1-piperidinyl)propyl]-N'-(4-chlorophenyl)-N-(4-methylbenzyl)urea trifluoroacetate Using the compound obtained in Reference Example 14, the title compound was synthesized in a manner similar to Example 30.

HPLC analysis (220 nm): purity 91% (Retention time 3.841 min).

MS (APCI$^+$) 490 (M+1).

EXAMPLE 43

N-[3-(4-Benzyl-1-piperidinyl)propyl]-N'-(4-chlorophenyl)-N-(4-methoxybenzyl)urea trifluoroacetate Using the compound obtained in Reference Example 15, the title compound was synthesized in a manner similar to Example 30.

HPLC analysis (220 nm): purity 95% (Retention time 3.521 min).

MS (APCI$^+$) 506 (M+1).

EXAMPLE 44

N-[3-(4-Benzyl-1-piperidinyl)propyl]-N-(2,6-difluorobenzyl)-N'-(4-methoxyphenyl)urea trifluoroacetate Using the compound obtained in Reference Example 11, the title compound was synthesized in a manner similar to Example 33.

HPLC analysis (220 nm): purity 99% (Retention time 3.511 min).

MS (APCI$^+$) 508 (M+1).

EXAMPLE 45

N-[3-(4-Benzyl-1-piperidinyl)propyl]-N-(2-chlorobenzyl)-N'-(4-methoxyphenyl)urea trifluoroacetate Using the compound obtained in Reference Example 12, the title compound was synthesized in a manner similar to Example 33.

HPLC analysis (220 nm): purity 99% (Retention time 3.469 min).

MS (APCI$^+$) 506 (M+1).

EXAMPLE 46

N-[3-(4-Benzyl-1-piperidinyl)propyl]-N-(4-chlorobenzyl)-N'-(4-methoxyphenyl)urea trifluoroacetate Using the compound obtained in Reference Example 13, the title compound was synthesized in a manner similar to Example 33.

HPLC analysis (220 nm): purity 99% (Retention time 3.475 min).

MS (APCI$^+$) 506 (M+1).

EXAMPLE 47

N-[3-(4-Benzyl-1-piperidinyl)propyl]-N'-(4-methoxyphenyl)-N-(4-methylbenzyl)urea trifluoroacetate Using the compound obtained in Reference Example 14, the title compound was synthesized in a manner similar to Example 33.

HPLC analysis (220 nm): purity 94% (Retention time 3.719 min).

MS (APCI$^+$) 486 (M+1).

EXAMPLE 48

N-[3-(4-Benzyl-1-piperidinyl)propyl]-N-(4-methoxybenzyl)-N'-(4-methoxyphenyl)urea trifluoroacetate Using the compound obtained in Reference Example 15, the title compound was synthesized in a manner similar to Example 33.

HPLC analysis (220 nm): purity 97% (Retention time 3.403 min).

MS (APCI$^+$) 502 (M+1).

EXAMPLE 49

N-[3-(4-Benzyl-1-piperidinyl)propyl]-N'-cyclohexyl-N-(2,6-difluorobenzyl)urea trifluoroacetate Using the compound obtained in Reference Example 11, the title compound was synthesized in a manner similar to Example 36.

HPLC analysis (220 nm): purity 88% (Retention time 3.549 min).

MS (APCI$^+$) 484 (M+1).

EXAMPLE 50

N-[3-(4-Benzyl-1-piperidinyl)propyl]-N-(2-chlorobenzyl)-N'-cyclohexylurea trifluoroacetate Using the compound obtained in Reference Example 12, the title compound was synthesized in a manner similar to Example 36.

HPLC analysis (220 nm): purity 98% (Retention time 3.521 min).

MS (APCI$^+$) 482 (M+1).

EXAMPLE 51

N-[3-(4-Benzyl-1-piperidinyl)propyl]-N-(4-chlorobenzyl)-N'-cyclohexylurea trifluoroacetate Using the compound obtained in Reference Example 13, the title compound was synthesized in a manner similar to Example 36.

HPLC analysis (220 nm): purity 99% (Retention time 3.515 min).

MS (APCI$^+$) 482 (M+1).

EXAMPLE 52

N-[3-(4-Benzyl-1-piperidinyl)propyl]-N'-cyclohexyl-N-(4-methylbenzyl urea trifluoroacetate Using the compound obtained in Reference Example 14, the title compound was synthesized in a manner similar to Example 36.

HPLC analysis (220 nm): purity 94% (Retention time 3.776 min).

MS (APCI$^+$) 462 (M+1).

EXAMPLE 53

N-[3-(4-Benzyl-1-piperidinyl)propyl]-N'-cyclohexyl-N-(4-methoxybenzyl)urea trifluoroacetate Using the compound obtained in Reference Example 15, the title compound was synthesized in a manner similar to Example 36.

HPLC analysis (220 nm): purity 100% (Retention time 3.448 min).

MS (APCI$^+$) 478 (M+1).

EXAMPLE 54

Ethyl {N'-Benzyl-N'-[3-(4-benzyl-1-piperidinyl)propyl]ureido}-acetate trifluoroacetate Using ethyl isocyanatoacetate, the title compound was synthesized in a manner similar to Example 14.

HPLC analysis (220 nm): purity 97% (Retention time 2.883 min).

MS (APCI$^+$) 452 (M+1).

EXAMPLE 55

N-Benzyl-N-[3-(4-benzyl-1-piperidinyl)propyl]-N'-tert-butylurea trifluoroacetate Using tert-butylisocyanate, the title compound was synthesized in a manner similar to Example 14.

HPLC analysis (220 nm): purity 99% (Retention time 3.531 min).

MS (APCI$^+$) 422 (M+1).

EXAMPLE 56

N-Benzyl-N-[3-(4-benzyl-1-piperidinyl)propyl]-N'-[(1S)-1-(1-naphthyl)ethyl]urea trifluoroacetate Using (1S)-1-(1-naphthyl)ethyl isocyanate, the title compound was synthesized in a manner similar to Example 14.

HPLC analysis (220 nm): purity 100% (Retention time 3.800 min).

MS (APCI$^+$) 520 (M+1).

EXAMPLE 57

N-Benzyl-N-[3-(4-benzyl-1-piperidinyl)propyl]-N'-hexylurea trifluoroacetate

Using hexyl isocyanate, the title compound was synthesized in a manner similar to Example 14.

HPLC analysis (220 nm): purity 99% (Retention time 3.732 min).

MS (APCI$^+$) 450 (M+1).

EXAMPLE 58

N-Benzyl-N-[3-(4-benzyl-1-piperidinyl)propyl]-N'-cyclohexylurea trifluoroacetate Using cyclohexyl isocyanate, the title compound was synthesized in a manner similar to Example 14.

HPLC analysis (220 nm): purity 99% (Retention time 3.598 min).

MS (APCI$^+$) 448 (M+1).

EXAMPLE 59

Diethyl (2S)-2-{N'-benzyl-N'-[3-(4-benzyl-1-piperidinyl)propyl]ureido}glutarate trifluoroacetate Using diethyl (2S)-2-isocyanatoglutarate, the title compound was synthesized in a manner similar to Example 14.

HPLC analysis (220 nm): purity 100% (Retention time 3.501 min).

MS (APCI$^+$) 552 (M+1).

EXAMPLE 60

N,N'-Dibenzyl-N-[3-(4-benzyl-1-piperidinyl)propyl]urea trifluoroacetate

Using benzyl isocyanate, the title compound was synthesized in a manner similar to Example 14.

HPLC analysis (220 nm): purity 100% (Retention time 3.491 min).

MS (APCI$^+$) 456 (M+1).

EXAMPLE 61

Methyl (2S)-2-{N'-benzyl-N'-[3-(4-benzyl-1-piperidinyl)propyl]-ureido}-4-methylpentanoate trifluoroacetate Using methyl (2S)-2-isocyanato-4-methylpentanoate, the title compound was synthesized in a manner similar to Example 14.

HPLC analysis (220 nm): purity 99% (Retention time 3.587 min).

MS (APCI$^+$) 494 (M+1).

EXAMPLE 62

N'-(1-Adamantyl)-N-benzyl-N-[3-(4-benzyl-1-piperidinyl)propyl]urea trifluoroacetate Using 1-adamantyl isocyanate, the title compound was synthesized in a manner similar to Example 14.

HPLC analysis (220 nm): purity 99% (Retention time 3.969 min).

MS (APCI$^+$) 500 (M+1).

EXAMPLE 63

N-Benzyl-N-[3-(4-benzyl-1-piperidinyl)propyl]-N'-(3-isopropenyl-α,α-dimethylbenzyl)urea trifluoroacetate Using 3-isopropenyl-α,α-dimethylbenzyl isocyanate, the title compound was synthesized in a manner similar to Example 14.

HPLC analysis (220 nm): purity 99% (Retention time 3.987 min).

MS (APCI$^+$) 524 (M+1).

EXAMPLE 64

N-Benzyl-N-[3-(4-benzyl-1-piperidinyl)propyl]-N'-propylurea trifluoroacetate

Using propyl isocyanate, the title compound was synthesized in a manner similar to Example 14.

HPLC analysis (220 nm): purity 99% (Retention time 3.318 min).

MS (APCI$^+$) 408 (M+1).

EXAMPLE 65

N-[3-(4-Benzyl-1-piperidinyl)propyl]-N'-(4-chlorophenyl)-N-(cyclohexylmethyl)urea trifluoroacetate Using the compound obtained in Reference Example 16, the title compound was synthesized in a manner similar to Example 30.

HPLC analysis (220 nm): purity 97%. (Retention time 3.917 min).

MS (APCI$^+$) 482 (M+1).

EXAMPLE 66

N-[3-(4-Benzyl-1-piperidinyl)propyl]-N'-(4-chlorophenyl)-N-(3-pyridylmethyl)urea trifluoroacetate Using the compound obtained in Reference Example 17, the title compound was synthesized in a manner similar to Example 30.

HPLC analysis (220 nm): purity 98% (Retention time 2.879 min).

MS (APCI$^+$) 477 (M+1).

EXAMPLE 67

N-[3-(4-Benzyl-1-piperidinyl)propyl]-N-(cyclohexylmethyl)-N'-(4-methoxyphenyl)urea trifluoroacetate Using the compound obtained in Reference Example 16, the title compound was synthesized in a manner similar to Example 33.

HPLC analysis (220 nm): purity 94% (Retention time 2.946 min).

MS (APCI$^+$) 478 (M+1).

EXAMPLE 68

N-[3-(4-Benzyl-1-piperidinyl)propyl]-N'-(4-methoxyphenyl)-N-(3-pyridylmethyl)urea trifluoroacetate Using the compound obtained in Reference Example 17, the title compound was synthesized in a manner similar to Example 33.

HPLC analysis (220 nm): purity 97% (Retention time 1.917 min).

MS (APCI$^+$) 473 (M+1).

EXAMPLE 69

N-[3-(4-Benzyl-1-piperidinyl)propyl]-N'-cyclohexyl-N-(cyclohexylmethyl)urea trifluoroacetate Using the compound obtained in Reference Example 16, the title compound was synthesized in a manner similar to Example 36.

HPLC analysis (220 nm): purity 100% (Retention time 3.842 min).

MS (APCI$^+$) 454 (M+1).

EXAMPLE 70

N-[3-(4-Benzyl-1-piperidinyl)propyl]-N'-cyclohexyl-N-(3-pyridylmethyl)urea trifluoroacetate Using the compound obtained in Reference Example 17, the title compound was synthesized in a manner similar to Example 36.

HPLC analysis (220 nm): purity 99% (Retention time 2.801 min).

MS (APCI$^+$) 449 (M+1).

EXAMPLE 71

N'-(4-Chlorophenyl)-N-(3-{4-[4-(4-morpholinylsulfonyl)benzyl]-1-piperidinyl}propyl)-N-phenylurea hydrochloride Using the compound obtained in Reference Example 18-4, the title compound was synthesized in a manner similar to Example 2.

Yield 54%.

$^1$H NMR (CD$_3$OD) δ 1.09–1.27 (1H, m), 1.49–1.74 (2H, m), 1.81–2.06 (4H, m), 2.75 (2H, d, J=6.6 Hz), 2.94 (4H, t, J=4.6 Hz), 3.19 (2H, t, J=6.4 Hz), 3.29–3.32 (2H, m), 3.55–3.62 (2H, m), 3.70 (4H, t, J=4.6 Hz), 3.86 (2H, t, J=6.4 Hz), 7.20–7.33 (5H, m), 7.40–7.58 (7H, m), 7.71 (2H, d, J=8.0 Hz).

EXAMPLE 72

N'-(4-Chlorophenyl)-N-(3-{4-[4-(4-methylsulfonyl)benzyl]-1-piperidinyl}propyl)-N-phenylurea hydrochloride Using the compound obtained in Reference Example 19-5, the title compound was synthesized in a manner similar to Example 2.

Yield 57%.

Free base: $^1$H NMR (CDCl$_3$) δ 1.23–2.18 (9H, m), 2.39–2.54 (2H, m), 2.62 (2H, d, J=5.6 Hz), 2.88–3.03 (2H, m), 3.05 (3H, s), 3.77 (2H, t, J=7.4 Hz), 6.43 (1H, s), 7.16–7.53 (11H, m), 7.85 (2H, d, J=8.4 Hz).

EXAMPLE 73

N-[3-(4-Benzyl-1-piperidinyl)propyl]-N'-(4-chlorophenyl)-N-(4-cyanophenyl)urea

Using the compound obtained in Reference Example 20, the title compound was synthesized in a manner similar to Example 2.

Yield 67%.

$^1$H NMR (CDCl$_3$) δ 1.20–1.40 (2H, m), 1.48–2.04 (7H, m), 2.28–2.60 (4H, m), 2.86–2.99 (2H, m), 3.91 (2H, t, J=6.2 Hz), 7.05–7.45 (11H, m), 7.68 (2H, d, J=8.8 Hz), 8.90 (1H, brs).

EXAMPLE 74

N-[3-(4-Benzyl-1-piperidinyl)propyl]-N'-(4-chlorophenyl)-N-(3-cyanophenyl)urea hydrochloride Using the compound obtained in Reference Example 21, the title compound was synthesized in a manner similar to Example 2.

Yield 57%.

Free base: $^1$H NMR (CDCl$_3$) δ 1.20–1.40 (2H, m), 1.45–1.81 (5H, m), 1.85–2.02 (2H, m), 2.04 (3H, s), 2.38–2.57 (4H, m), 2.85–2.98 (2H, m), 3.83 (2H, t, J=6.4 Hz), 7.07–7.40 (11H, m), 7.44–7.60 (2H, m), 8.53 (1H, brs).

EXAMPLE 75

N-[3-(4-Benzyl-1-piperidinyl)propyl]-N'-(4-chlorophenyl)-N-(3-pyridinyl)urea hydrochloride 4-Chlorophenyl isocyanate (297 mg) was added to a solution of N-[3-(4-benzyl-1-piperidinyl)propyl]-3-pyridineamine (400 mg) in tetrahydrofuran (5 ml) and the mixture was stirred for 15 hours. Ethyl acetate (15 ml) and saturated sodium bicarbonate (15 ml) were added to the reaction mixture. The organic phase was separated, washed with water (10 ml) and saturated brine (10 ml) and dried over sodium sulfate (anhydrous), and the solvent was removed. The residue was purified by silica gel column chromatography (20 g). The fraction eluted by ethyl acetate-methanol (10:1) was collected and concentrated under reduced pressure. A solution of 4N hydrogen chloride in ethyl acetate (1.0 ml) was added to the residue. The precipitate was filtered and collected, and dried under reduced pressure to give the title compound (555 mg, Yield 76.0%).

Free base: $^1$H NMR (CDCl$_3$) δ 1.43–1.86 (9H, m), 2.43 (2H, t, J=6.6 Hz), 2.51 (2H, d, J=6.2 Hz), 2.90 (3H, m), 3.82 (2H, t, J=6.6 Hz), 7.09–7.40 (10H, m), 7.64 (1H, m), 8.01 (1H, bs), 8.52–8.58 (2H, m).

EXAMPLE 76

N-[3-(4-Benzyl-1-piperidinyl)propyl]-N'-(4-chlorophenyl)-N-phenylurea hydrochloride Using 4-chlorophenyl isocyanate, the title compound was synthesized in a manner similar to Example 1. Yield 60%.

$^1$H NMR (DMSO-d$_6$) δ 1.3–2.0 (7H, m), 2.45–2.6 (2H, m), 2.6–3.5 (6H, m), 3.65–3.8 (2H, m), 7.1–7.55 (14H, m), 8.08 (1H, s).

EXAMPLE 77

4-{[1-(3-{[(4-Chloroanilino)carbonyl]anilino}propyl)-4-piperidinyl]methyl}benzamide Using the compound obtained in Reference Example 23-6, the title compound was synthesized in a manner similar to Example 2.

Yield 58%.

$^1$H NMR (CDCl$_3$) δ 1.17–1.39 (2H, m), 1.40–1.90 (7H, m), 2.32–2.39 (2H, m), 2.56 (2H, d, J=5.8 Hz), 2.83–2.88 (2H, m), 3.73–3.80 (2H, m), 5.40–6.20 (2H, br), 6.58 (1H, brs), 7.16–7.51 (11H, m), 7.14 (2H, d, J=8.6 Hz).

TEST EXAMPLE (1) Cloning of Human CCR5 Chemokine Receptor

Cloning of CCR5 gene was carried out by PCR (polymerase chain reaction) from human spleen cDNA. With using 0.5 ng of spleen cDNA (Toyobo, QUICK-Clone cDNA) as a template, PCR was performed in DNA Thermal Cycler 480 (Perkin-Elmer) (reaction conditions: 30 cycles of 95° C. for 1 minute, 60° C. for 1 minute, and 75° C. for 5 minutes) by adding primer set, 5'-CAGGATCCGATGGATTATCAAGTGTCAAGTCCAA-3' (25 pmol) and 5'-TCTAGATCACAAGCCCACAGATATTTCCTGCTCC- 3' (25 pmol), which were designed referring to nucleotide sequence of CCR5 gene reported by Samson et al. (Biochemistry, 35 (11), 3362–3367 (1996)) and by using TaKaRa EX Taq (Takara Shuzo). The resultant PCR product was subjected to agarose gel electrophoresis to collect about 1.0 kb DNA fragment, which was subjected to Original TA Cloning Kit (Funakoshi) to carry out cloning of CCR5 gene.
(2) Preparation of Plasmid for Expression of Human CCR5

The plasmid obtained in the above (1) was digested with restriction enzymes XbaI (Takara Shuzo) and BamHI (Takara Shuzo) and subjected to agarose gel electrophoresis to collect about 1.0 kb DNA fragment. The DNA fragment was mixed with plasmid pcDNA3.1 (Funakoshi) for expression in animal cells, said plasmid being digested with XbaI and BamHI, and they were ligated with DNA Ligation Kit Ver.2 (Takara Shuzo). The resulting plasmid was subjected to transformation of competent cell of E. coli JM109 (Takara Shuzo) to give plasmid pCKR5.
(3) Introduction of Plasmid for Expression of Human CCR5 into CHO-K1 Cell and Expression of the Plasmid in CHO-K1 Cell CHO-K1 cells were grown in 750 ml of tissue culture flask (Becton Dickinson) using Ham's F12 medium (Nihon Pharmaceutical) containing 10% fetal calf serum (Life Tech Oriental) and took off with 0.5 g/L trypsin-0.2 g/L EDTA (Life Tech Oriental). The cells were washed with PBS (Life Tech Oriental), centrifuged (1000 rpm, 5 minutes), and suspended in PBS. With using Gene Pulser (Bio-Rad Laboratories), DNA was introduced into the cells under the conditions shown below. That is, to the cuvette having 0.4 cm gap were added $8 \times 10^6$ cells and 10 µg of plasmid pCKR5 for expression of human CCR5, and electroporation was carried out under 0.25 kV of voltage and 960 µF of capacitance. The cells were transferred into Ham's F12 medium containing 10% fetal calf serum, and cultivated for 24 hours. The cells were again took off and centrifuged, and suspended in Ham's F12 medium containing 10% fetal calf serum and 500 µg/ml of geneticin (Life Tech Oriental). The suspension was diluted to give $10^4$ cells/ml of the suspension, which was inoculated on 96 well plate (Becton Dickinson) to give geneticin resistant cells.

Then, the resulting geneticin resistant cells were cultivated in 96 well plate (Becton Dickinson), and cells expressing CCR5 were selected from the geneticin resistant cells. That is, in an assay buffer (Ham's F12 medium containing 0.5% BSA and 20 mM HEPES (Wako Pure Chemical, pH 7.2) to which was added 200 pM of [$^{125}$I]-RANTES (Amersham) as a ligand, binding reaction was carried out at room temperature for 40 minutes, and the buffer was washed with ice-cooled PBS. To the buffer was added 50 µl/well of 1M NaOH, and the mixture was stirred. Radioactivity was determined with γ-counter to select CHO/CCR5 cells which specifically bound with the ligand.
(4) Evaluation of Test Compounds Based on CCR5 Antagonistic Activity The CHO/CCR5 were inoculated on 96 well microplate ($5 \times 10^4$ cells/well) and cultivated for 24 hours. The medium was removed by means of suction, and to each well was added assay buffer containing Test Compound (1 µl) and then 100 pM of [$^{125}$I]-RANTES (Amersham) as a ligand. The reaction was carried out at room temperature for 40 minutes, and assay buffer was removed by means of suction. Each well was washed twice with cooled PBS, and 200 µl of Microscinti-20 (Packard Instrument, Inc.) was added to each well. Radioactivity was determined with Top-Count Micro Scintillation Counter (Packard Instrument, Inc.).

According to the method described above, the inhibition rate of the test compounds for CCR5 binding was determined.

The results are shown in Table 1.

| Example Number | Inhibition Rate (%) at 1.0 µM |
|---|---|
| 1 | 96 |
| 7 | 92 |
| 10 | 100 |
| 12 | 92 |
| 13 | 67 |
| 71 | 98 |
| 72 | 94 |

(5) Inhibitory Effect on HIV-1 Infection to MAGI-CCR5 Cell

The plasmid where β-galactosidase gene was ligated to the downstream of HIV-1 LTR was introduced into CD4 positive HeLa cell, to which human CCR$^5$ was further introduced to obtain transformant MAGI-CCR5. By using said transformant MAGI-CCR5, the degree of HIV-1 infection was calculated from β-galactosidase activity (blue color due to decomposition of 5-bromo-4-chloro-3-indolyl-β-D-galactopyranoside). Specifically, MAGI-CCR5 cells were suspended in DMEM medium containing 10% serum to prepare $5 \times 10^4$ cells/ml suspension. To each well of 96 well plate was inoculated 200 µl of the suspension, and the cells were cultivated at 37° C. overnight. The medium was removed by means of suction, and to the residue was added 100 µl of the above medium containing 0.32 µM of Test Compound and 100 µl of the above medium containing 300PFU of HIV-1 Ba-L cells. The final concentration of the test compound was 0.16 µM. The cells were cultivated at 37° C. for 2 days. The medium was removed by means of suction. To the residue was added 200 µl of cell fixative (PBS containing 1% formaldehyde and 0.2% glutaraldehyde), and the mixture was allowed to stand at room temperature for 5 minutes and washed twice with PBS. To the mixture was added 100 µl of staining solution (PBS containing 4 µM potassium ferrocyanide, 4 µM potassium ferricyanade, 2 µM MgCl$_2$ and 0.4 mg/ml X-gal), and the mixture was allowed to stand at 37° C. for 50 minutes and washed twice with PBS. The number of blue cells was counted by microscope and defined as the number of cells infected with HIV-1. According to this method, inhibition rate on HIV-1 infection was determined and found that Compounds obtained from Example 76 shows 98% inhibition on HIV-1 infection.

The pharmaceutical composition for antagonizing CCR5 (e.g. a medicament for the treatment or prevention of infectious disease of HIV, a medicament for the treatment or prevention of AIDS, etc.) comprising the compound (I) of the present invention, as an active ingredient, can be prepared, for example, by the following prescriptions:

| Preparations 1. Capsule | |
|---|---|
| (1) Compound obtained in Working Example 1 | 40 mg |
| (2) Lactose | 70 mg |
| (3) Fine crystalline cellulose | 9 mg |
| (4) Magnesium stearate | 1 mg |
| 1 capsule | 120 mg |

(1), (2), (3) and ½ of (4) are mixed and then granulated. To the granules is added the remainder of (4), and the whole is filled into a gelatin capsule.

| 2. Tablet | |
|---|---|
| (1) Compound obtained in Working Example 10 | 40 mg |
| (2) Lactose | 58 mg |
| (3) Corn starch | 18 mg |
| (4) Fine crystalline cellulose | 3.5 mg |
| (5) Magnesium stearate | 0.5 mg |
| 1 tablet | 120 mg |

(1), (2), (3), ⅔ of (4) and ½ of (5) are mixed and then granulated. To the granules are added the remainders of (4) and (5), followed by subjecting the mixture to compression molding.

INDUSTRIAL APPLICABILITY

The compound of the formula (I) or salt thereof of the present invention has superior CCR5 antagonistic activity and can be advantageously used for the treatment or prevention of various infectious disease of HIV in human (e.g. AIDS).

What is claimed is:

1. A compound of the formula:

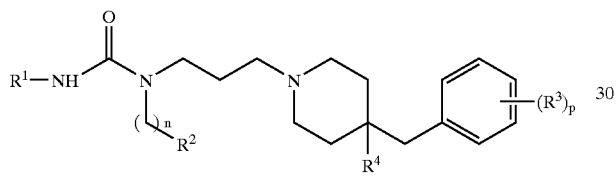

(I)

wherein $R^1$ is an aryl group which may be substituted;

$R^2$ is a cyclic hydrocarbon group which may be substituted or a heterocyclic group which may be substituted;

$R^3$ is a carbamoyl group which may be substituted, a sulfamoyl group which may be substituted, or an acyl group derived from a sulfonic acid;

$R^4$ is a hydrogen atom or a hydroxy group;

n is an integer of 0;

p is an integer of 0 or 1 to 4;

or a salt thereof.

2. The compound as claimed in claim 1, wherein $R^1$ is an aryl group which may be substituted by 1 to 4 substituent(s) selected from 1) a hydrocarbon group which may be substituted, 2) a heterocyclic group which may be substituted, 3) a $C_{1-4}$ alkoxy group which may be substituted, 4) a $C_{1-4}$ alkylthio group which may be substituted, 5) a $C_{2-6}$ alkoxycarbonyl group which may be substituted, 6) a $C_{1-6}$ alkanoyl group which may be substituted, 7) an amino group which may be substituted, 8) a cyclic amino group, 9) a halogen atom, 10) a nitro group, 11) a cyano group, 12) a carbamoyl group which may be substituted, 13) a sulfamoyl group which may be substituted and 14) an acyl group derived from a sulfonic acid.

3. The compound as claimed in claim 1, wherein $R^1$ is an aryl group which may be substituted by 1 to 4 substituent(s) selected from 1) a hydrocarbon group which may be substituted, 2) a heterocyclic group which may be substituted, 3) a $C_{1-4}$ alkoxy group which may be substituted, 4) a $C_{1-4}$ alkylthio group which may be substituted, 5) a $C_{2-6}$ alkoxycarbonyl group which may be substituted, 6) an amino group which may be substituted, 7) a halogen atom, 8) a nitro group and 9) a cyano group.

4. The compound as claimed in claim 1, wherein $R^1$ is an aryl group which may be substituted by 1 to 4 substituent(s) selected from 1) a hydrocarbon group which may be substituted, 2) a heterocyclic group which may be substituted, 3) a $C_{1-4}$ alkylthio group, which may be substituted, 4) a $C_{2-6}$ alkoxycarbonyl group which may be substituted, 5) an amino group which may be substituted, 6) a halogen atom and 7) a nitro group.

5. The compound as claimed in claim 1, wherein $R^1$ is an aryl group which may be substituted by member(s) selected from Group 1;

$R^2$ is a cyclic hydrocarbon group selected from Group 10 which may be substituted by member(s) selected from Group 2, or a heterocyclic group selected from Group 4 which may be substituted by member(s) selected from Group 2;

$R^3$ is a carbamoyl group, a N-mono-substituted carbamoyl group which is substituted by a member selected from Group 11, a N,N-di-substituted carbamoyl group which is substituted by a member selected from Group 11 and a member selected from Group 14, a cyclic aminocarbonyl group selected from Group 17, a sulfamoyl group, N-mono-substituted sulfamoyl group which is substituted by a member selected from Group 11, a N,N-di-substituted sulfamoyl group which is substituted by a member selected from Group 11 and a member selected from Group 14, a cyclic aminosulfonyl group selected from Group 20, or an acyl group derived from a sulfonic acid selected from Group 15, wherein Group 1 includes 1) a hydrocarbon group selected from Group 3 which may be substituted by member(s) selected from Group 2, 2) a heterocyclic group selected from Group 4 which may be substituted by member(s) selected from Group 2, 3) a $C_{1-4}$ alkoxy group which may be substituted by member(s) selected from Group 2, 4) a $C_{1-4}$ alkylthio group which may be substituted by member(s) selected from Group 2, 5) a $C_{2-6}$ alkoxycarbonyl group which may be substituted by member(s) selected from Group 2, 6) a $C_{1-6}$ alkanoyl group, 7) an amino group which may be substituted by member(s) selected from Group 8, 8) a cyclic amino group selected from Group 9, 9) a halogen atom, 10) a nitro group, 11) a cyano group, 12) a carbamoyl group, 13) a mono-substituted carbamoyl group which is substituted by a member selected from Group 11, 14) di-substituted carbamoyl group which is substituted by a member selected from Group 11 and a member selected Group 14, 15) a cyclic amino carbamoyl group selected from Group 17, 16) a sulfamoyl group, 17) a N-mono substituted sulfamoyl group which is substituted by a member selected from Group 11, 18) a N,N-di-substituted sulfamoyl group which is substituted by a member selected from Group 11 and a member selected Group 14, and 19) an acyl group derived from a sulfonic acid selected from Group 19, Group 2 includes 1) a $C_{1-6}$ alkoxy group, 2) a halogen atom, 3) a $C_{1-6}$ alkyl group, 4) a $C_{1-4}$ alkenyl group, 5) an amino group, 6) a hydroxy group, 7) a cyano group and 8) an amidino group, Group 3 includes
1) a $C_{1-6}$ alkyl group, 2) a $C_{3-8}$ cycloalkyl group and 3) a $C_{6-14}$ aryl group, Group 4 includes
1) an aromatic monocyclic heterocyclic group selected from Group 5, 2) an aromatic condensed heterocyclic group selected from Group 6 and 3) a saturated or unsaturated non-aromatic heterocyclic group selected from Group 7, Group 5 includes furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, Group 6 includes
benzofuranyl, isobenzofuranyl, benzothienyl, indolyl, isoindolyl, 1H-indazolyl, benzindazolyl, benzoxazolyl, 1,2-benzisoxazolyl, benzothiazolyl, benzopyranyl, 1,2-benzisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, Group 7 includes
oxyranyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl, Group 8 includes
1) a $C_{1-6}$ alkyl, 2) a $C_{1-6}$ alkanoyl, 3) a $C_{7-13}$ arylcarbonyl, 4) an optionally halogenated $C_{2-6}$ alkoxycarbonyl, 5) a $C_{1-6}$ alkylimidoyl, 6) a formylimidoyl and 7) an amidino, Group 9 includes
1) 1-azetidinyl, 2) 1-pyrrolidinyl, 3) 1-piperidinyl, 4) 4-morpholinyl, 5) 1-piperazinyl and 6) 1-piperazinyl which may have a $C_{1-6}$ alkyl, a $C_{7-10}$ aralkyl or a $C_{610}$ aryl at 4-position, Group 10 includes
a $C_{3-9}$ cycloalkyl, 1-indanyl, 2-indanyl, $C_{3-6}$ cycloalkenyl, $C_{4-6}$ cycloalkanedienyl and $C_{6-14}$ aryl, Group 11 includes
1) a $C_{1-6}$ alkyl group which may be substituted by member(s) selected from Group 12, 2) a $C_{3-6}$ cycloalkyl group which may be substituted by member(s) selected from Group 12, 3) a $C_{6-10}$ aryl group which may be substituted by member(s) selected from Group 12, 4) a $C_{7-10}$ aralkyl group which may be substituted by member(s) selected from Group 12, 5) a $C_{1-6}$ alkoxy group which may be substituted by member(s) selected from Group 12 and 6) a heterocyclic group selected from Group 13 which may be substituted by member(s) selected from Group 12, Group 12 includes
1) a hydroxy group, 2) an amino group, 3) an amino group which is mono or di-substituted by member(s) selected from Group 16, 4) a halogen atom, 5) a nitro group, 6) a cyano group, 7) a $C_{1-6}$ alkyl group which may be substituted by halogen atom(s) and 8) a $C_{1-6}$ alkoxy group which may be substituted by halogen atom(s), Group 13 includes
1) an aromatic heterocyclic group selected from Group 5 and Group 6 and 2) a saturated or unsaturated non aromatic heterocyclic group selected from Group 7, each of which contains at least one heteroatom(s) selected from the group consisting of an oxygen atom, a sulfur atom and a nitrogen atom, Group 14 includes
a $C_{1-6}$ alkyl group, a $C_{3-6}$ cycloalkyl group and a $C_{7-10}$ aralkyl group, Group 15 includes
1) a $C_{1-10}$ to alkylsulfonyl which may be substituted by member(s) selected from Group 12, 2) a $C_{2-6}$ alkenylsulfonyl which may be substituted by member(s) selected from Group 12, 3) a $C_{2-6}$ alkynylsulfonyl which may be substituted by member(s) selected from Group 12, 4) a $C_{3-9}$ cycloalkylsulfonyl which may be substituted by member(s) selected from Group 12, 5) a $C_{3-9}$ cycloalkenylsulfonyl which may be substituted by member(s) selected from Group 12, 6) a $C_{6-14}$ arylsulfonyl which may be substituted by member(s) selected from Group 12 and 7) a $C_{7-10}$ aralkylsulfonyl which may be substituted by member(s) selected from Group 12, Group 16 includes
a $C_{1-6}$ alkyl group, a $C_{1-6}$ alkanoyl, a $C_{7-13}$ arylcarbonyl and a $C_{1-6}$ alkylsulfonyl, Group 17 includes
1-azetidinylcarbonyl, 1-pyrrolidinylcarbonyl, 1-piperidinylcarbonyl, 4-morpholinylcarbonyl and 1-piperazinylcarbonyl which may be substituted by member(s) selected from Group 18, Group 18 includes
a $C_{1-6}$ alkyl group, a $C_{7-10}$ aralkyl group and a $C_{6-10}$ aryl group, Group 19 includes
a $C_{1-10}$ alkylsulfonyl which may be substituted by member(s) selected from Group 12, a $C_{2-6}$ alkenylsulfonyl which may be substituted by member(s) selected from Group 12, a $C_{2-6}$ alkynylsulfonyl which may be substituted by member(s) selected from Group 12, a $C_{3-9}$ cycloalkylsulfonyl which may be substituted by member(s) selected from Group 12, a $C_{3-9}$ cycloalkenylsulfonyl which may be substituted by member(s) selected from Group 12, a $C_{6-14}$ arylsulfonyl which may be substituted by member(s) selected from Group 12, and a $C_{7-10}$ aralkylsulfonyl which may be substituted by member(s) selected from Group 12, and Group 20 includes
1-azetidinylsulfonyl, 1-pyrrolidinylsulfonyl, 1-piperidinylsulfonyl, 4-morpholinylsulfonyl and 1-piperazinylsulfonyl which may be substituted by member(s) selected from Group 18.

6. The compound as claimed in claim 5, wherein $R^1$ is a $C_{6-14}$ aryl group which may be substituted by member(s) selected from Group 1.

7. The compound as claimed in claim 5, wherein
$R^1$ is a $C_{6-14}$ aryl group which may be substituted by a halogen atom, a $C_{1-6}$ alkyl which may be substituted by halogen(s), a $C_{1-4}$ alkylthio, a nitro, a carbamoyl, a sulfamoyl or $C_{1-6}$ alkylsulfonyl;

$R^2$ is a phenyl group which may be substituted by a halogen atom, a $C_{1-6}$ alkyl, a $C_{1-4}$ alkoxy or a cyano, a $C_{3-8}$ cycloalkyl group or a pyridyl group;

$R^3$ is (i) a carbamoyl group, (ii) a sulfamoyl group which may have one or two of $C_{1-6}$ alkyl(s) and $C_{3-6}$ cycloalkyl(s) at N-atoms, (iii) a cyclic aminosulfonyl group which is selected from Group 20, (iv) a $C_{1-6}$ alkylsulfonyl group, or (v) $C_{3-6}$ cycloalkylsulfonyl group;

$R^4$ is a hydrogen atom;

n is 0, and p is 0 or 1.

8. The compound as claimed in claim 5, wherein $R^1$ is 1) a phenyl group which may be substituted by a halogen atom, a $C_{1-3}$ alkyl, trifluoromethyl, methoxy, trifluoromethoxy, methylthio or nitro, or 2) a naphthyl, $R^2$ is a phenyl group which may be substituted by a halogen atom, methyl, methoxy or cyano, a cyclohexyl group or a 3-pyridyl group;

$R^3$ is (i) a carbamoyl group, (ii) a 4-morpholinylsulfonyl group or (iii) a methylsulfonyl group;

$R^4$ is a hydrogen atom;

n is 0; and p is 0 or 1.

9. The compound as claimed in claim 5, wherein $R^1$ is a phenyl group which may be substituted by a halogen atom or a $C_{1-3}$ alkyl;

$R^2$ is a phenyl group which may be substituted by halogen atom or methyl(s);

$R^3$ is (i) a carbamoyl group, (ii) a sulfamoyl group which may be substituted at N-atoms by one or two members selected from $C_{1-6}$ alkyl and $C_{3-6}$ cycloalkyl, (iii) a cyclic aminosulfonyl group selected from Group 20, (iv) a $C_{1-6}$ alkylsulfonyl group or (v) a $C_{3-6}$ cycloalkyl sulfonyl group;

$R^4$ is a hydrogen atom;

n is 0; and p is 0 or 1.

10. N-[3-(4-benzyl-1-piperidinyl)propyl]-N'-4-chlorophenyl)-N-phenylurea,

N'-(4-chlorophenyl)-N-(3-{4-[4-(4-morpholinylsulfonyl)benzyl]-1-piperidinyl}propyl)-N-phenylurea, N'-(4-chlorophenyl)-N-(3-{4-[4-(4-methylsulfonyl)benzyl]-1-piperidinyl}propyl)-N-phenylurea or 4-{[1-(3-{[(4-chloroanilino)carbonyl]anilino}propyl)-4-piperidinyl]methyl}benzamide, or a salt thereof.

11. A prodrug of a compound of the formula:

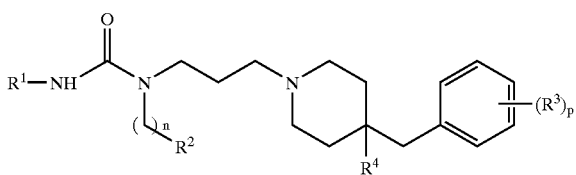

(I)

wherein $R^1$ is an aryl group which may be substituted;

$R^2$ is a cyclic hydrocarbon group which may be substituted or a heterocyclic group which may be substituted;

$R^3$ is a carbamoyl group which may be substituted, a sulfamoyl group which may be substituted, or an acyl group derived from a sulfonic acid, $R^4$ is a hydrogen atom or a hydroxy group;

n is an integer of 0;

p is an integer of 0 or 1 to 4;

or salt thereof.

* * * * *